(12) United States Patent
Jacobsen et al.

(10) Patent No.: US 11,168,056 B2
(45) Date of Patent: Nov. 9, 2021

(54) PROCESS FOR THE MANUFACTURING OF (6AR,10AR)-7-PROPYL-6,6A,7,8,9,10,10A,11-OCTAHYDRO-[1,3]DIOXOLO[4',5':5,6] BENZO[1,2-G]QUINOLINE AND (4AR,10AR)-1-PROPYL-1,2,3,4,4A,5,10,10A-OCTAHYDRO-BENZO[G]QUINOLINE-6,7-DIOL

(71) Applicant: H. Lundbeck A/S, Valby (DK)

(72) Inventors: Mikkel Fog Jacobsen, Valby (DK); Martin Juhl, Valby (DK); Frans Dennis Therkelsen, Valby (DK); Kåre Søndergaard, Valby (DK); Tobias Gylling Frihed, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/876,966

(22) Filed: May 18, 2020

(65) Prior Publication Data

US 2020/0369615 A1 Nov. 26, 2020

(30) Foreign Application Priority Data

May 20, 2019 (DK) .............................. PA201900600

(51) Int. Cl.
*C07D 215/06* (2006.01)
*C07D 317/60* (2006.01)

(52) U.S. Cl.
CPC ......... *C07D 215/06* (2013.01); *C07D 317/60* (2013.01)

(58) Field of Classification Search
None
See application file for complete search history.

(56) References Cited

U.S. PATENT DOCUMENTS

| | | | |
|---|---|---|---|
| 4,543,256 | A | 9/1985 | Neumeyer |
| 4,565,818 | A | 1/1986 | Nordmann et al. |
| 4,692,453 | A | 9/1987 | Seiler |
| 5,747,513 | A | 5/1998 | Montanari et al. |
| 5,885,988 | A | 3/1999 | Neumann et al. |
| 5,955,468 | A | 9/1999 | Markstein |
| 8,129,530 | B2 | 3/2012 | Jorgensen et al. |
| 10,729,710 | B2 | 8/2020 | Jensen et al. |
| 2009/0062324 | A1 | 3/2009 | Jorgensen et al. |
| 2012/0077836 | A1 | 3/2012 | Wilkstrom et al. |
| 2017/0335357 | A1 | 11/2017 | Divi et al. |
| 2020/0338102 | A1 | 1/2020 | Balmer et al. |
| 2020/0369705 | A1 | 11/2020 | Juhl et al. |
| 2020/0369706 | A1 | 11/2020 | Juhl et al. |
| 2020/0392176 | A1 | 12/2020 | Jensen et al. |

FOREIGN PATENT DOCUMENTS

| | | |
|---|---|---|
| CN | 102746351 A | 10/2012 |
| CN | 105218606 A | 1/2016 |
| GB | 2 192 394 A | 1/1998 |
| JP | S60-172975 A | 9/1985 |
| WO | WO 90/12574 A1 | 11/1990 |
| WO | WO 97/03054 A1 | 1/1997 |
| WO | WO 98/38155 A1 | 9/1998 |
| WO | WO 00/47571 A1 | 8/2000 |
| WO | WO 01/36428 A1 | 5/2001 |
| WO | 2001/078713 A1 | 10/2001 |
| WO | WO 01/76602 A1 | 10/2001 |
| WO | WO 2001/078713 A1 | 10/2001 |
| WO | WO 02/13827 A1 | 2/2002 |
| WO | 2002/100377 A1 | 12/2002 |
| WO | WO 2002/100377 A1 | 12/2002 |
| WO | WO 03/006458 A1 | 1/2003 |
| WO | WO 03/013532 A1 | 2/2003 |

(Continued)

OTHER PUBLICATIONS

Bibbiani et al., Continuous dopaminergic stimulation reduces risk of motor complications in parkinsonian primates. Exp Neurol. Mar. 2005;192(1):73-8. doi: 10.1016/j.expneurol.2004.11.013.

Campbell et al., Behavioral effects of (-)10,11-methylenedioxy-N-n-propylnoraporphine, an orally effective long-acting agent active at central dopamine receptors, and analogous aporphines. Neuropharmacology. Oct. 1982;21(10):953-61. doi: 10.1016/0028-3908(82)90106-x.

Giardina et al., Adrogolide HCl (ABT-431; DAS-431), a prodrug of the dopamine D1 receptor agonist, A-86929: preclinical pharmacology and clinical data. CNS Drug Rev. 2001 Fall;7(3):305-16. doi: 10.1111/j.1527-3458.2001.tb00201.x.

(Continued)

*Primary Examiner* — Zinna Northington Davis
(74) *Attorney, Agent, or Firm* — Wolf, Greenfield & Sacks, P.C.

(57) ABSTRACT

The present invention relates to a new process for manufacturing (6aR,10aR)-7-propyl-6,6a,7,8,9,10,10a,11-octahydro-[1,3]dioxolo[4',5':5,6]benzo[1,2-g]quinoline with formula (Ib) below, (4aR,10aR)-1-Propyl-1,2,3,4,4a,5,10,10a-octahydro-benzo[g]quinoline-6,7-diol with formula (I) below and salts thereof.

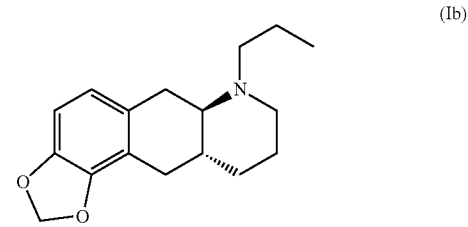

(Ib)

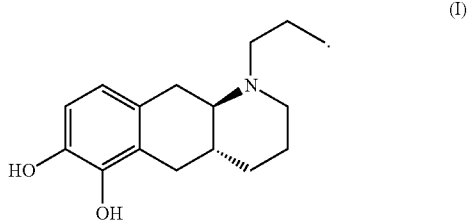

(I)

Both compounds are for use in the treatment of neurodegenerative diseases and disorders such as Parkinson's Disease. The invention also relates to new intermediate compounds of said process.

13 Claims, No Drawings

(56) References Cited

FOREIGN PATENT DOCUMENTS

| | | |
|---|---|---|
| WO | WO 03/074511 A1 | 9/2003 |
| WO | WO 03/080074 A1 | 10/2003 |
| WO | WO 2005/062894 A2 | 7/2005 |
| WO | WO 2006/012640 A2 | 2/2006 |
| WO | WO 2006/056604 A1 | 6/2006 |
| WO | 2009/026934 A1 | 3/2009 |
| WO | 2009/026935 A1 | 3/2009 |
| WO | WO 2009/026934 A1 | 3/2009 |
| WO | WO 2009/026935 A1 | 3/2009 |
| WO | 2010/097092 A1 | 9/2010 |
| WO | WO 2010/097092 A1 | 9/2010 |
| WO | WO 2013/020979 A1 | 2/2013 |
| WO | WO 2013/034119 A1 | 3/2013 |
| WO | WO 2015/067927 A1 | 5/2015 |
| WO | WO 2017/184871 A1 | 10/2017 |
| WO | 2019/101917 A1 | 5/2019 |
| WO | WO 2019/101917 A1 | 5/2019 |

OTHER PUBLICATIONS

Liu et al., A novel synthesis and pharmacological evaluation of a potential dopamine D1/D2 agonist: 1-propyl-l,2,3,4,4a,5,10,10a-octahydrobenzo[g]quinoline-6,7-diol. Bioorg Med Chem. Mar. 15, 2008;16(6):3438-44. doi: 10.1016/j.bmc.2007.06.036. Epub Jun. 23, 2007.

Liu et al., Extremely potent orally active benzo[g]quinoline analogue of the dopaminergic prodrug: 1-propyl-trans-2,3,4,4a,5,7,8,9,10,10a-decahydro-lH-benzo-[g]quinolin-6-one [corrected]. J Med Chem. Feb. 23, 2006;49(4): 1494-8. doi: 10.1021/jm051111h.

Poewe et al., Parkinson disease. Nat Rev Dis Primers. Mar. 23, 2017;3:17013. doi: 10.1038/nrdp.2017.13.

Rothman et al., Evidence for possible involvement of 5-HT(2B) receptors in the cardiac valvulopathy associated with fenfluramine and other serotonergic medications. Circulation. Dec. 5, 2000;102(23):2836-41. doi: 10.1161/01.cir. 102.23.2836.

International Search Report and Written Opinion for Application No. PCT/EP2018/082361 dated Feb. 22, 2019.

International Search Report and Written Opinion for Application No. PCT/EP2020/063909 dated Jul. 2, 2020.

International Search Report and Written Opinion for Application No. PCT/EP2020/063910 dated Jul. 14, 2020.

International Search Report and Written Opinion for Application No. PCT/EP2020/063908 dated Sep. 11, 2020.

Ahari et al., A direct stereoselective approach to trans-2,3-disubstituted piperidines: application in the synthesis of 2-Epi-CP-99,994 and (+)-epilupinine. Org Lett. Jun. 19, 2008; 10(12):2473-6. doi: 10.1021/ol800722a. Epub May 14, 2008.

Billeter et al., 8-Hydroxyflavonoid Glucuronides from Malva Sylvestris. Phytochemistry. 1991;30(3):987-90.

Brown et al., Structurally constrained hybrid derivatives containing octahydrobenzo[g or f]quinoline moieties for dopamine D2 and D3 receptors: binding characterization at D2/D3 receptors and elucidation of a pharmacophore model. J Med Chem. Dec. 25, 2008;51(24):7806-19. doi: 10.1021/jm8008629.

Fan et al., Modifications of the isonipecotic acid fragment of SNS-032: analogs with improved permeability and lower efflux ratio. Bioorg Med Chem Lett. Dec. 1, 2008; 18(23):6236-9. doi: 10.1016/j.bmcl.2008.09.099. Epub Oct. 2, 2008.

Fumeaux et al., First synthesis, characterization, and evidence for the presence of hydroxycinnamic acid sulfate and glucuronide conjugates in human biological fluids as a result of coffee consumption. Org Biomol Chem. Nov. 21, 2010;8(22):5199-211. doi: 10.1039/c0ob00137f. Epub Sep. 14, 2010.

Knobloch et al., Keto Esters Derived from 2-(Trimethylsilyl) ethanol: An Orthogonal Protective Group for β-Keto Esters. Synthesis 2008.14 (2008): 2229-2246.

Loozen et al., An approach to the synthesis of [2] benzopyrano [3, 4?c] pyrroles; alternative dopaminergic molecules. Recueil des Travaux Chimiques des Pays?Bas. 1982; 101(9):298-310.

Morissette et al., High-throughput crystallization: polymorphs, salts, co-crystals and solvates of pharmaceutical solids. Adv Drug Deliv Rev. Feb. 23, 2004;56(3):275-300. doi: 10.1016/j.addr.2003.10.020.

ZHANG et al., Flavonoid metabolism: the synthesis of phenolic glucuronides and sulfates as candidate metabolites for bioactivity studies of dietary flavonoids. Tetrahedron. 2012; 68:4194-4201.

U.S. Appl. No. 16/876,908, filed May 18, 2020, Allowed, 2020-0369706.

U.S. Appl. No. 16/876,908, filed May 18, 2020, Published, 2020-0392176.

PCT/EP2018/082361, Feb. 22, 2019, International Search Report and Written Opinion.

PCT/EP2020/063909, Jul. 2, 2020, International Search Report and Written Opinion.

PCT/EP2020/063910, Jul. 14, 2020, International Search Report and Written Opinion.

PCT/EP2020/063908, Sep. 11, 2020, International Search Report and Written Opinion.

U.S. Appl. No. 16/198,917, filed Nov. 23, 2018, Granted, U.S. Pat. No. 10,729,710.

U.S. Appl. No. 16/872,802, filed May 12, 2020, Allowed, 2020-0338102.

U.S. Appl. No. 16/876,843, filed May 18, 2020, Allowed, 2020-0369705.

U.S. Appl. No. 16/876,878, filed May 18, 2020, Allowed, 2020-069706.

U.S. Appl. No. 16/876,908, filed May 18, 2020, Allowed, 2020-0392176.

International Search Report and Written Opinion dated Jul. 15, 2020 in connection with Application No. PCT/EP2020/063913.

Alexander et al., Functional architecture of basal ganglia circuits: neural substrates of parallel processing. Trends Neurosci. Jul. 1990;13(7):266-71. doi: 10.1016/0166-2236(90)90107-1.

Bibbiani et al., Continuous dopaminergic stimulation reduces risk of motor complications in parkinsonian primates. Exp Neurol. Mar. 2005;192(l):73-8. doi: 10.1016/j.expneurol.2004.11.013.

Campbell et al., Behavioral effects of (-)10,ll-methylenedioxy-N-n-propylnoraporphine, an orally effective long-acting agent active at central dopamine receptors, and analogous aporphines. Neuropharmacology. Oct. 1982;21(10):953-61. doi: 10.1016/0028-3908(82)90106-x.

Cannon et al., N?Alkyl derivatives of trans?6, 7?dihydroxy?l, 2, 3, 4, 4a, 5, 10, 10b?octahyrobenzo [g] quinoline A congener of apomorphine lacking the non?oxygenated aromatic ring. J Heterocycl Chem. Nov. 1980; 17(7): 1633-6.

Cavero et al., Safety Pharmacology assessment of drugs with biased 5-HT(2B) receptor agonism mediating cardiac valvulopathy. J Pharmacol Toxicol Methods. Mar.-Apr. 2014;69(2):150-61. doi: 10.1016/j.vascn.2013.12.004. Epub Dec. 19, 2013.

Delong et al., Primate models of movement disorders of basal ganglia origin. Trends Neurosci. Jul. 1990;13(7):281-5. doi: 10.1016/0166-2236(90)90110-v.

Fan et al., Differential effects of pro-BDNF on sensory neurons after sciatic nerve transection in neonatal rats. Eur J Neurosci. May 2008;27(9):2380-90. doi: 10.1111/j.1460-9568.2008.06215.x. Epub Apr. 22, 2008.

Gerfen et al., DI and D2 dopamine receptor-regulated gene expression of striatonigral and striatopallidal neurons. Science. Dec. 7, 1990;250(4986): 1429-32. doi: 10.1126/science.2147780.

Giardina et al., Adrogolide HCl (ABT-431; DAS-431), a prodrug of the dopamine DI receptor agonist, A-86929: preclinical pharmacology and clinical data. CNS Drug Rev. 2001 Fall;7(3):305-16. doi: 10.1111/j. 1527-3458.2001.tb00201.x.

Goswami et al., Intestinal absorption and metabolism of retinoyl beta-glucuronide in humans, and of 15-[14C]-retinoyl beta-glucuronide in rats of different vitamin A status. J Nutr Biochem. Dec. 2003;14(12):703-9. doi: 10.1016/j.jnutbio.2003.08.008.

Grosset et al., Inhaled dry powder apomorphine (VR040) for 'off' periods in Parkinson's disease: an in-clinic double-blind dose ranging study. Acta Neurol Scand. Sep. 2013; 128(3): 166-71. doi: 10.1111/ane.l2107. Epub Mar. 26, 2013.

(56) References Cited

OTHER PUBLICATIONS

Hauser et al., Sublingual apomorphine (APL-130277) for the acute conversion of OFF to ON in Parkinson's disease. Mov Disord. Sep. 2016;31(9): 1366-72. doi: 10.1002/mds.26697. Epub Jul. 19, 2016.

Kotsuki et al., Highly practical, enantiospecific synthesis of the cyclohexyl fragment of the immunosuppressant FK-506. J Org Chem. Aug. 1992;57(18):5036-40.

Liu et al., A novel synthesis and pharmacological evaluation of a potential dopamine D1/D2 agonist: 1-propyl-1,2,3,4,4a,5,10,10a-octahydrobenzo[g]quinoline-6,7-diol. Bioorg Med Chem. Mar. 1, 20085;16(6):3438-44. doi: 10.1016/j.bmc.2007.06.036. Epub Jun. 23, 2007.

Liu et al., Extremely potent orally active benzo[g]quinoline analogue of the dopaminergic prodrug: 1-propyl-trans-2,3,4,4a,5,7,8,9,10,10a-decahydro-1H-benzo-[g]quinolin-6-one [corrected]. J Med Chem. Feb. 2, 20063;49(4): 1494-8. doi: 10.1021/jm051111h.

Nolen et al., Budesonide-beta-D-glucuronide: a potential prodrug for treatment of ulcerative colitis. J Pharm Sci. Jun. 1995;84(6):677-81. doi: 10.1002/jps.2600840603.

Poewe et al., Parkinson disease. Nat Rev Dis Primers. Mar. 2, 20173;3:17013. doi: 10.1038/nrdp.2017.13.

Rothman et al., Evidence for possible involvement of 5-HT(2B) receptors in the cardiac valvulopathy associated with fenfluramine and other serotonergic medications. Circulation. 2000 Dec5;102(23):2836-41. doi: 10.1161/01.cir. 102.23.2836.

Sozio et al., Designing prodrugs for the treatment of Parkinson's disease. Expert Opin Drug Discov. May 2012;7(5):385-406. doi: 10.1517/17460441.2012.677025. Epub Apr. 12, 2012.

Sprenger et al., Management of motor and non-motor symptoms in Parkinson's disease. CNS Drugs. Apr. 2013;27(4):259-72. doi: 10.1007/s40263-013-0053-2.

Stain-Texier et al., Intestinal absorption and stability of morphine 6-glucuronide in different physiological compartments of the rat. Drug Metab Dispos. May 1998;26(5):383-7.

PROCESS FOR THE MANUFACTURING OF (6AR,10AR)-7-PROPYL-6,6A,7,8,9,10,10A,11-OCTAHYDRO-[1,3]DIOXOLO[4',5':5,6]BENZO[1,2-G]QUINOLINE AND (4AR,10AR)-1-PROPYL-1,2,3,4,4A,5,10,10A-OCTAHYDRO-BENZO[G]QUINOLINE-6,7-DIOL

CROSS-REFERENCE TO RELATED APPLICATIONS

This application claims priority to Danish Application No. PA201900600, filed May 20, 2019, the entire contents of the aforementioned applications are hereby incorporated herein by reference.

FIELD OF THE INVENTION

The present invention relates to a process for manufacturing (4aR,10aR)-1-Propyl-1,2,3,4,4a,5,10,10a-octahydro-benzo[g]quinoline-6,7-diol and (6aR,10aR)-7-propyl-6,6a,7,8,9,10,10a,11-octahydro-[1,3]dioxolo[4',5':5,6]benzo[1,2-g]quinoline and salts thereof which are compounds for use in the treatment of neurodegenerative diseases and disorders such as Parkinson's Disease. The invention also relates to new intermediates of said process.

BACKGROUND OF THE INVENTION

Parkinson's disease (PD) is a common neurodegenerative disorder that becomes increasingly prevalent with age and affects an estimated seven to ten million people worldwide. Parkinson's disease is a multi-faceted disease characterized by both motor and non-motor symptoms. Motor symptoms include resting tremor (shaking), bradykinesia/akinesia (slowness and poverty of movements), muscular rigidity, postural instability and gait dysfunction; whereas non-motor symptoms include neuropsychiatric disorders (e.g. depression, psychotic symptoms, anxiety, apathy, mild-cognitive impairment and dementia) as well as autonomic dysfunctions and sleep disturbances (Poewe et al., Nature Review, (2017) vol 3 article 17013: 1-21).

A key hallmark of Parkinson's disease pathophysiology is the loss of pigmented dopaminergic neurons in the substantia nigra pars compacta that provides dopaminergic innervation to the striatum and other brain areas. Such progressive neurodegeneration leads to the decrease in dopamine striatal levels which ultimately results in a series of changes in the basal ganglia circuitry, ultimately ending up in the occurrence of the four cardinal motor features of Parkinson's disease. The main target of dopamine in the striatum consists of medium spiny GABAergic neurons (MSNs) selectively expressing D1 or D2 receptors pending topographical projections. GABAergic-MSN projecting to the external pallidum, also called striato-pallidal 'indirect pathway' express D2 receptors (MSN-2); whereas GABAergic-MSN projecting to the substantia nigra pars reticulata and internal pallidum, also called striato-nigral 'direct pathway' express D1 receptors (MSN-1). Depletion of dopamine because of neuronal loss results in an imbalanced activity of the two pathways, resulting in a marked reduction of thalamic and cortical output activities and ultimately motor dysfunctions (Gerfen et al, Science (1990) 250: 1429-32; Delong, (1990) Trends in Neuroscience 13: 281-5; Alexander et Crutcher, (1990) Trends in Neuroscience 13: 266-71; and for review Poewe et al., Nature Review (2017) vol. 3 article 17013: 1-21).

The most effective therapeutic strategies available to patients suffering from Parkinson's disease, and aiming at controlling motor symptoms are primarily indirect and direct dopamine agonists. The classic and gold standard treatment regimen includes chronic oral intake of L-3,4-dihydroxyphenylalanine (L-DOPA) which is decarboxylated in the brain to form dopamine. Other approaches consist in the administration of dopamine receptor agonists such as apomorphine which acts both on the D1 and D2 receptors subtypes, or pramipexole, ropinirole and others which are predominantly directed towards D2 receptors subtypes. Acceptable motor relief is obtained with use of both L-DOPA and apomorphine due to their activation of both D1 and D2 receptor subtypes and holistic re-equilibrium of the indirect-direct pathways (i.e. while D2 agonists only reverse the indirect pathway dysfunction).

L-DOPA and apomorphine with the structures depicted below are currently the most efficacious PD drugs in clinical use.

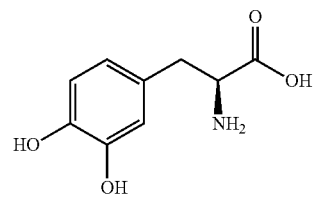

L-DOPA

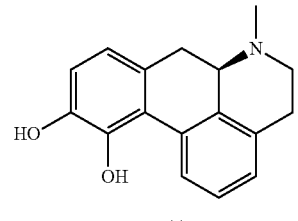

apomorphine

L-DOPA is a prodrug of dopamine and remains the most efficacious drug in the treatment of motor Parkinson's disease. However, after several years of treatment (i.e. the honeymoon period), complications arise due the inherent progression of the disease (i.e. sustained loss of dopaminergic neurons) as well as poor pharmacokinetic (PK) profile of L-DOPA. Those complications include: 1) dyskinesia which are abnormal involuntary movements occurring during the optimal 'on-time effect' of the drug; and 2) off fluctuations, period during which the L-DOPA positive effect wears off and symptoms re-emerge or worsen (Sprenger and Poewe, CNS Drugs (2013), 27: 259-272).

Direct dopamine receptor agonists are able to activate the dopamine autoreceptors as well as the postsynaptic dopamine receptors located on the medium spiny neurons MSN-1 and MSN-2. Apomorphine belongs to a class of dopamine agonists with a 1,2-dihydroxybenzene (catechol) moiety. When combined with a phenethylamine motif, catecholamines often possess low or no oral bioavailability as is the case for apomorphine. Apomorphine is used clinically in PD therapy albeit with a non-oral delivery (typically intermittent subcutaneous administration or daytime continuous parenteral infusion via a pump). For apomorphine, animal studies have shown that transdermal delivery or implants may provide possible forms of administration. However, when the delivery of apomorphine from implants was studied in monkeys (Bibbiani et al., Chase Experimental Neurology (2005), 192: 73-78) it was found that in most cases the animals had to be treated with the immunosuppressant Dexamethasone to prevent local irritation and other complications following the implantation surgery. Alternative delivery strategies for apomorphine therapy in PD such as inhalation and sublingual formulations have been extensively explored (see e.g. Grosset et al., Acta Neurol Scand. (2013), 128:166-171 and Hauser et al., Movement Disorders (2016), Vol. 32 (9): 1367-1372). However, these efforts are yet not in clinical use for the treatment of PD.

An alternative to the non-oral formulations of the catecholamines involves the use of a prodrug masking the free catechol hydroxyl groups to enable oral administration. However, a known problem associated with the development of prodrugs for clinical use is the difficulties associated with predicting conversion to the parent compound in humans.

Various ester prodrugs of catecholamines have been reported in the literature such as enterically coated N-propyl-noraporphine (NPA) and the mono pivaloyl ester of apomorphine for duodenal delivery (see eg. WO 02/100377), and the D1-like agonist adrogolide, a diacetyl prodrug of A-86929 (Giardina and Williams; CNS Drug Reviews (2001), Vol. 7 (3): 305-316). Adrogolide undergoes extensive hepatic first-pass metabolism in man after oral dosing and, as a result, has a low oral bioavailability (app. 4%). In PD patients, intravenous (IV) Adrogolide has antiparkinson efficacy comparable to that of L-DOPA (Giardina and Williams; CNS Drug Reviews (2001), Vol. 7 (3): 305-316).

In addition to the ester prodrugs of catecholamines, an alternative prodrug approach involves the masking of the two catechol hydroxyl groups as the corresponding methylene-dioxy derivative or di-acetalyl derivative. This prodrug principle has been described for example in Campbell et al., Neuropharmacology (1982); 21(10): 953-961 and in U.S. Pat. No. 4,543,256, WO 2009/026934 and WO 2009/026935.

Yet another suggested approach for a catecholamine prodrug is the formation of an enone derivative as suggested in for example WO 2001/078713 and in Liu et al., Bioorganic Med. Chem. (2008), 16: 3438-3444. For further examples of catecholamine prodrugs see for example Sozio et al., Exp. Opin. Drug Disc. (2012); 7(5): 385-406.

The compound (4aR,10aR)-1-propyl-1,2,3,4,4a,5,10,10a-octahydro-benzo[g]quinoline-6,7-diol depicted as compound (I) below is disclosed in WO 2009/026934. The trans-isomer was disclosed previously in Liu et al., J. Med. Chem. (2006), 49: 1494-1498 and then in Liu et al., Bioorganic Med. Chem. (2008), 16: 3438-3444 including pharmacological data indicating that the compound has a low oral bioavailability in rats. The racemate was disclosed for the first time in Cannon et al., J. Heterocyclic Chem. (1980); 17: 1633-1636.

Compound (I) is a dopamine receptor agonist with mixed D1 and D2 activity. Three prodrug derivatives of compound (I) are known in the art.

Liu et al., J. Med. Chem. (2006), 49: 1494-1498 and Liu et al., Bioorganic Med. Chem. (2008), 16: 3438-3444 disclose the enone derivative of formula (Ia) depicted below which was shown to be converted to the active compound (I) in rats.

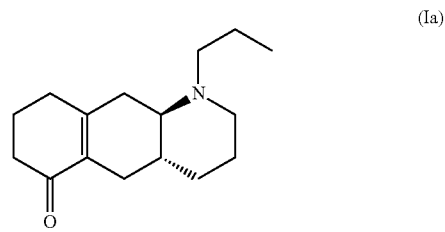 [SMILES: CCCN1CCC[C@@H]2CC3=C(CCCC3=O)C[C@H]21]

(Ia)

WO2009/026934 and WO2009/026935 disclose two types of prodrug derivatives of compound (I) including a compound (6aR,10aR)-7-propyl-6,6a,7,8,9,10,10a,11-octahydro-[1,3]dioxolo[4',5':5,6]benzo[1,2-g]quinoline with the formula (Ib) below:

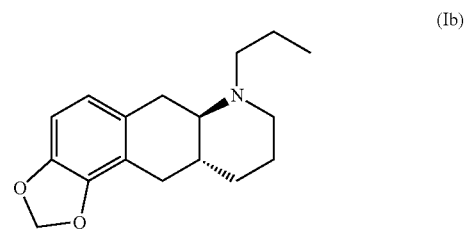 [SMILES: CCCN1CCC[C@@H]2Cc3c(ccc4c3OCO4)C[C@H]21]

(Ib)

The conversion of compound (Ib) to compound (I) in rat and human hepatocytes has been demonstrated in WO2010/097092. Furthermore, the in vivo pharmacology of the compounds (Ia) and (Ib) as well as the active "parent compound" (I) has been tested in various animal models relevant for Parkinson's Disease (WO2010/097092). Both compound (I) and compounds (Ia) and (Ib) were found to be effective, indicating that compounds (Ia) and (Ib) are converted in vivo to compound (I). All three compounds were reported to have a duration of action that was longer than observed for L-dopa and apomorphine.

The other prodrug of compound (I) disclosed in WO2009/026934 and WO2009/026935 is a conventional ester prodrug of the formula (Ic):

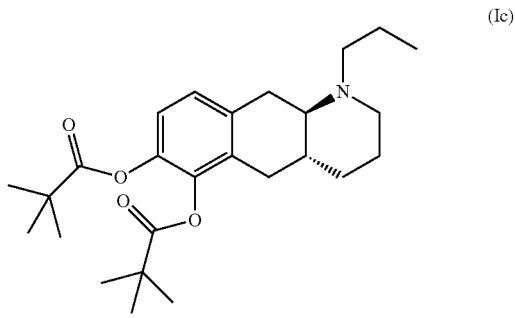 [SMILES: CCCN1CCC[C@@H]2Cc3c(ccc(OC(=O)C(C)(C)C)c3OC(=O)C(C)(C)C)C[C@H]21]

(Ic)

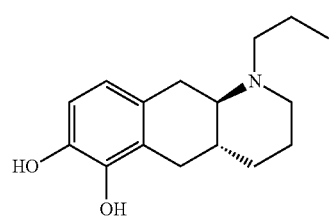

(I)

Despite the long-standing interest in the field, there is evidently still an unmet need as regards developing efficient, well-tolerated and active drugs for the treatment of PD.

Consequently, there is also a need for a process for manufacturing of such drugs, in particular processes suitable for large scale production resulting in high yield of the products.

WO2009/026934 discloses a process for preparing compound (I) and a process for preparing compound (Ib) from compound (I). These processes include numerous steps and the use of chiral chromatography to obtain separate enantiomers and is thus not optimal for large scale production.

Thus, there is still a need for improved processes for large scale production of compound (I) and (Ib).

SUMMARY OF THE INVENTION

The inventors of the present invention have developed a new process for manufacturing (4aR,10aR)-1-Propyl-1,2,3,4,4a,5,10,10a-octahydro-benzo[g]quinoline-6,7-diol (compound (I)) and (6aR,10aR)-7-propyl-6,6a,7,8,9,10,10a,11-octahydro-[1,3]dioxolo[4',5':5,6]benzo[1,2-g]quinoline (compound (Ib)). The invented process for the manufacture of compound (I) offers several advantages compared to the previously described process in WO2009/026934 including 1) a short synthetic route, 2) improved overall yield of compound (I), 3) use of resolution via diastereomeric salts instead of resolution by supercritical fluid chromatography (SFC), the latter being uneconomical and not suitable for large scale production and 4) resolution at the early stage of the synthetic route instead of late stage resolution as described in WO2009/026934, which reduces amount of reagents/solvents needed and amount of waste generated.

One aspect of the invention relates to a new process for manufacturing (4aR,10aR)-1-Propyl-1,2,3,4,4a,5,10,10a-octahydro-benzo[g]quinoline-6,7-diol with formula (I) below and salts thereof (I)

from the compound (6aR,10aR)-7-propyl-6,6a,7,8,9,10,10a,11-octahydro-[1,3]dioxolo[4',5':5,6]benzo[1,2-g]quinoline with formula (Ib) below (Ib)

Another aspect of the invention also provides to a new process for manufacturing (6aR,10aR)-7-propyl-6,6a,7,8,9,10,10a,11-octahydro-[1,3]dioxolo[4',5':5,6]benzo[1,2-g]quinoline (compound (Ib) and salts thereof.

Further individual aspects relate to new intermediates of the process. Thus, one aspect of the invention provides the compound of formula (A2) below, or a salt thereof.

(A2)

Another aspect of the invention provides the compound of formula (A3) below or a salt thereof.

(A3)

Yet another aspect of the invention provides the compound of formula (A4) below or a salt thereof.

(A4)

Yet another aspect of the invention provides the compound of formula (A5) below or a salt thereof.

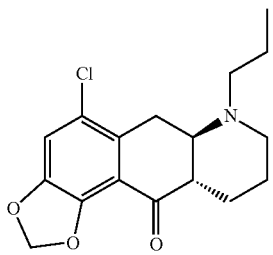

(A5)

Yet another embodiment of the invention provides a compound of formula (a2i) below or a salt thereof.

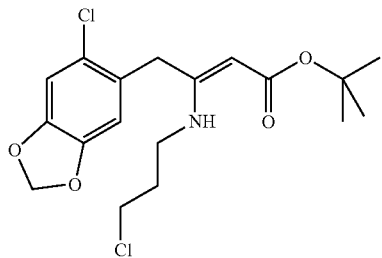

(a2i)

Yet another aspect of the invention provides a compound of formula (a2ii) below or a salt thereof.

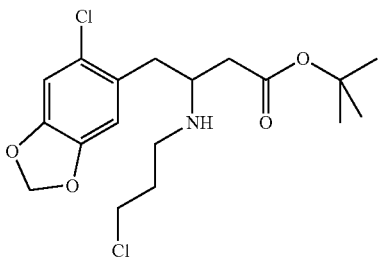 [SMILES: CC(C)(C)OC(=O)C[C@@H](Cc1cc2c(cc1Cl)OCO2)NCCCCl]

(a2ii)

Definitions

References to Compounds

References to compound (I), compound (Ib), compound (A1), compound (A2), compound (A3), compound (A4) or compound (A5) include the compounds in solution and solid forms of the compounds including the free substance (e.g. zwitter ion) of said compounds, salts of said compounds, such as acid addition salts or base addition salts, and polymorphic and amorphic forms of compounds of the invention and of salts thereof. Furthermore, said compounds and salts thereof may potentially exist in unsolvated as well as in solvated forms with solvents such as water, ethanol and the like.

Sometimes, a specific salt form is indicated for a compound, such as for example (A2-hemi-L-tartrate) which indicates the hemi-L-tartrate salt of compound (A2). Reference to compound compound (I), compound (Ib), compound (A1), compound (A2), compound (A3), compound (A4) or compound (A5) as a "free base" in the present context is intended to indicate said compound is in a non-salt form.

Pharmaceutically Acceptable Salts

Pharmaceutically acceptable salts in the present context is intended to indicate non-toxic, i.e. physiologically acceptable salts.

The term "pharmaceutically acceptable salts" include pharmaceutically acceptable acid addition salts which are salts formed with inorganic and/or organic acids on the nitrogen atom in the parent molecule. Said acids may be selected from for example hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, malonic acid, fumaric acid, glutamic acid, pyroglutamic acid, salicylic acid, gentisic acid, saccharin, and sulfonic acids such as methanesulfonic acid, ethanesulfonic acid, toluenesulfonic acid, naphthalene-2-sulphonic acid, 2-hydroxy ethanesulphonic acid and benzenesulfonic acid.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Compounds (Ib), (A1), (A2), (A3), (A4) and (A5) may be used as intermediates for the manufacture of compound (I), or a pharmaceutically acceptable salt thereof. Hence, the salt form of compounds (Ib), (A1), (A2), (A3), (A4) and (A5) are not limited to pharmaceutically acceptable salts thereof. Nevertheless, pharmaceutically acceptable salts of compounds (Ib), (A1), (A2), (A3), (A4) and (A5) can also advantageously be used in the manufacture of compound (I). Hence, in an embodiment of the invention the salt of compound (Ib), (A1), (A2), (A3), (A4) and/or (A5) is a pharmaceutically acceptable salt.

Chemical Manufacturing

In the present context, a compound "derived by chemical manufacturing" indicates that said compound has been manufactured by a chemical process ex vivo such as, but not limited to, one of the processes described in the experimental section herein. The wording "manufacture" and "chemical manufacturing" are used interchangeably.

Hence, in an embodiment of the invention compound (I) is manufactured by a chemical process ex vivo.

In a further embodiment of the invention compound (Ib) is manufactured by a chemical process ex vivo.

DETAILED DESCRIPTION OF THE INVENTION

The present invention relates to a new method for the manufacture of (4aR,10aR)-1-propyl-1,2,3,4,4a,5,10,10a-octahydro-benzo[g]quinoline-6,7-diol (compound (I)) going through the compound (6aR,10aR)-7-propyl-6,6a,7,8,9,10,10a,11-octahydro-[1,3]dioxolo[4',5':5,6]benzo-[1,2-g]quinoline (compound (Ib)). The invention also relates to a new process for the manufacture of compound (Ib).

Compound (Ib) is a prodrug of compound (I), which is a dual dopamine agonist with mixed D1 and D2 activity useful in the treatment of neurodegenerative diseases and disorders such as Parkinson's Disease. WO 2009/026934 discloses a process for the manufacture of compound (I) and a further process for the manufacture of compound (Ib) from compound (I).

The present inventors have found a new and improved method for the manufacture of both compounds wherein compound (Ib) is used as an intermediate in the manufacture of compound (I).

The overall process is illustrated in brief in Scheme 1 below.

The starting material (A1): tert-butyl 4-(6-chlorobenzo[d][1,3]dioxol-5-yl)-3-oxobutanoate can be made using known methods, such as described by Brückner and co-workers in *Synthesis* 2008, 14: 2229-2246, or as described below.

The starting material (a5i): 2-(benzo[d][1,3]dioxol-5-yl) acetonitrile is commercially available.

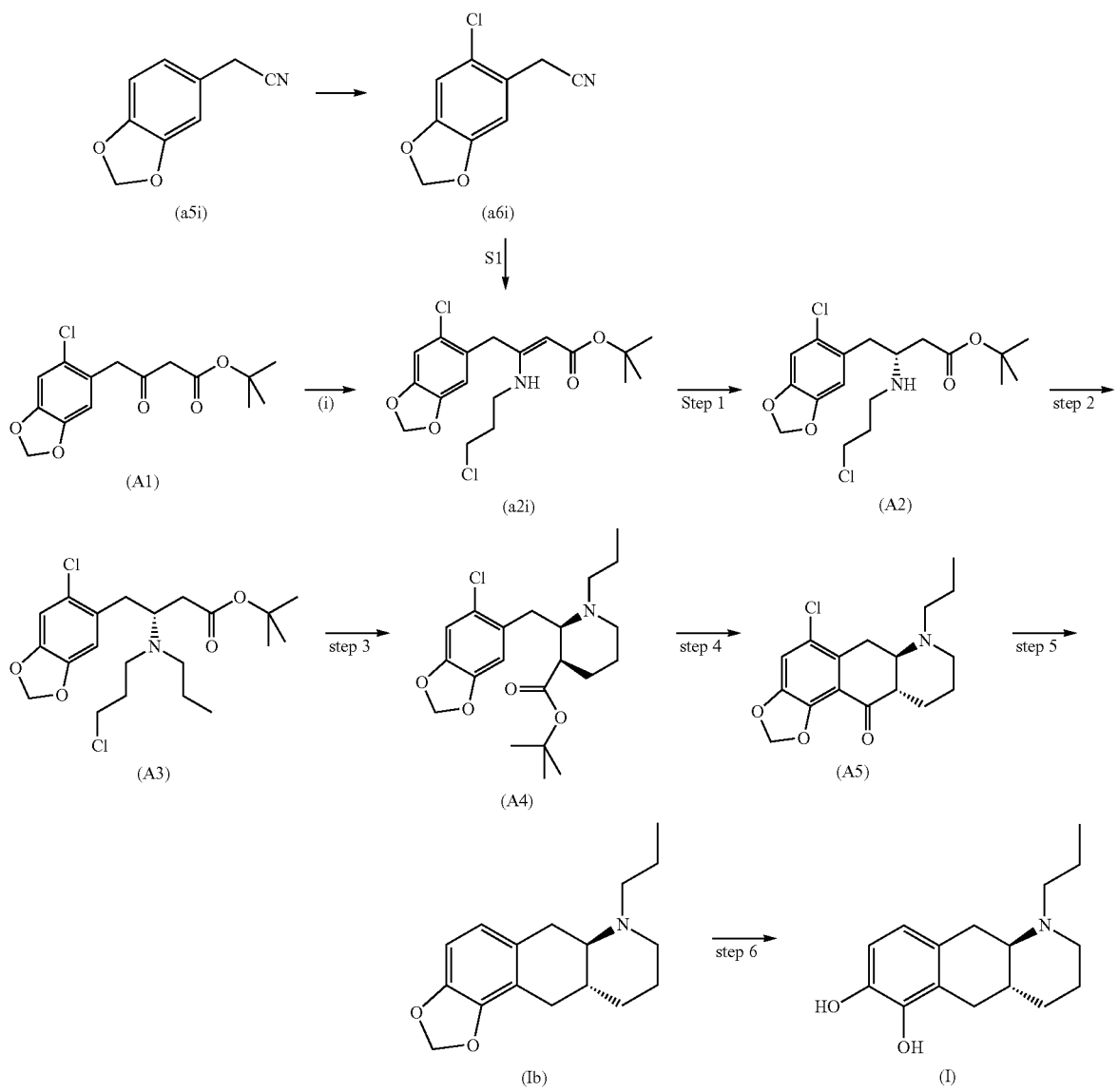
Scheme 1: Overall process
TABLE 1
List of names of isolated intermediates and other compounds:
| Compound abbreviation | Chemical name | Chemical structure |
|---|---|---|
| (A2) | tert-butyl(R)-4-(6-chlorobenzo[d][1,3]dioxol-5-yl)-3-((3-chloropropyl)amino)butanoate | (A2) |

TABLE 1-continued

List of names of isolated intermediates and other compounds:

| Compound abbreviation | Chemical name | Chemical structure |
|---|---|---|
| (A2-hemi-L-tartrate) | hemi-L-tartrate salt of compound (A2) | 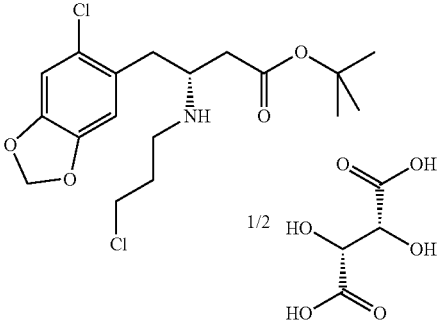<br>(A2-hemi-L-tartate) |
| (A3) | tert-butyl(R)-4-(6-chlorobenzo[d][1,3]dioxol-5-yl)-3-((3-chloropropyl)(propyl)amino)butanoate | 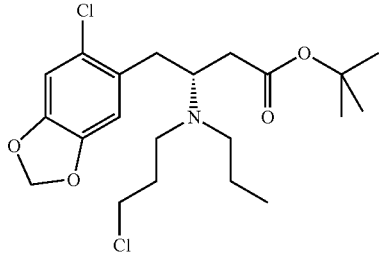 [SMILES: CCCN(CCCCl)[C@@H](CC(=O)OC(C)(C)C)Cc1cc2c(cc1Cl)OCO2]<br>(A3) |
| (A4) | Cis-tert-butyl(2R,3R)-2-((6-chlorobenzo[d][1,3]dioxol-5-yl)methyl)-1-propylpiperidine-3-carboxylate | 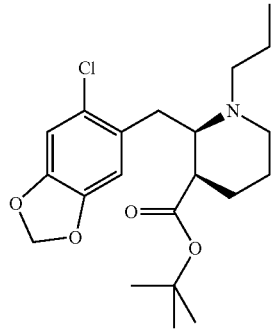 [SMILES: CCCN1CCC[C@@H](C(=O)OC(C)(C)C)[C@H]1Cc1cc2c(cc1Cl)OCO2]<br>(A4) |
| (A4-hemi-oxalate) | hemi-oxalate salt of compound (A4) | 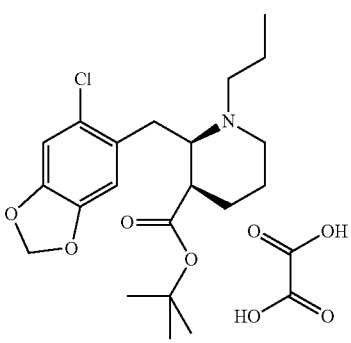<br>(A4-hemi-oxalate) |

TABLE 1-continued

List of names of isolated intermediates and other compounds:

| Compound abbreviation | Chemical name | Chemical structure |
|---|---|---|
| (A4-HCl) | HCl salt of compound (A4) | 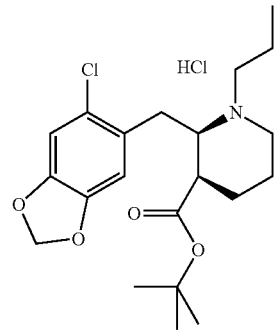 [SMILES: CCCN1CCC[C@@H](C(=O)OC(C)(C)C)[C@H]1Cc1cc2c(cc1Cl)OCO2 ; Cl] (A4-HCl) |
| (A5) | Trans-(6aR,10aS)-5-chloro-7-propyl-6a,7,8,9,10,10a-hexahydro-[1,3]dioxolo[4',5':5,6]benzo[1,2-g]quinolin-11(6H)-one | 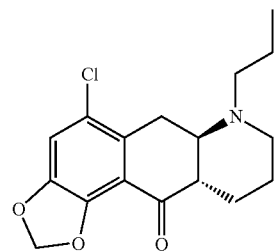 [SMILES: CCCN1CCC[C@@H]2C(=O)c3c(c(Cl)cc4c3OCO4)C[C@H]21] (A5) |
| (A5-tosylate) | p-toluenesulfonate salt of (A5) | 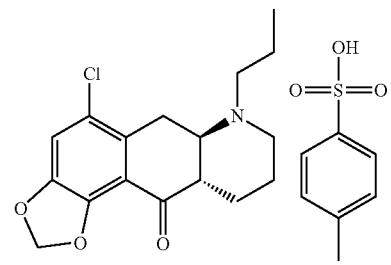 (A5-tosylate) |
| (A6) | Trans-5-chloro-7-propyl-6a,7,8,9,10,10a-hexahydro-[1,3]dioxolo[4',5':5,6]benzo[1,2-g]quinolin-11(6H)-one | 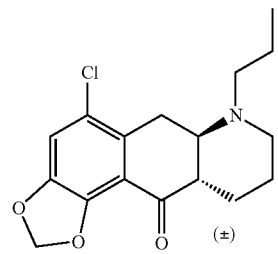 [SMILES: CCCN1CCC[C@@H]2C(=O)c3c(c(Cl)cc4c3OCO4)C[C@H]21] (A6) |

TABLE 1-continued

List of names of isolated intermediates and other compounds:

| Compound abbreviation | Chemical name | Chemical structure |
|---|---|---|
| (A6-tosylate) | p-toluenesulfonate salt of (A6) | (A6-tosylate) |
| (A7) | Trans-5-chloro-7-propyl-6,6a,7,8,9,10,10a,11-octahydro-[1,3]dioxolo[4',5':5,6]benzo[1,2-g]quinolin-11-ol | A7 |
| (A8) | Trans-7-propyl-6,6a,7,8,9,10,10a,11-octahydro-[1,3]dioxolo[4',5':5,6]benzo[1,2-g]quinolin-11-ol | A8 |
| (Ib-L-DTTA) | (−)-O,O'-di-p-toluoyl-L-tartaric acid salt of (Ib) | (Ib)-L-DTTA |
| (a2i) | tert-butyl(Z)-4-(6-chlorobenzo[d][1,3]dioxol-5-yl)-3-((3-chloropropyl)amino)but-2-enoate | 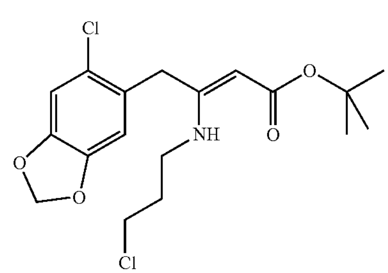 [SMILES: CC(C)(C)OC(=O)/C=C(/Cc1cc2c(cc1Cl)OCO2)NCCCCl] |

TABLE 1-continued

List of names of isolated intermediates and other compounds:

| Compound abbreviation | Chemical name | Chemical structure |
|---|---|---|
| (a2ii) | tert-butyl 4-(6-chlorobenzo[d][1,3]dioxol-5-yl)-3-((3-chloropropyl)amino)butanoate | (a2ii) |
| (a3i) | tert-butyl 3-(azetidin-1-yl)-4-(6-chlorobenzo[d][1,3]dioxol-5-yl)butanoate | (a3i) |
| (a3ii) | tert-butyl(R)-3-(azetidin-1-yl)-4-(6-chlorobenzo[d][1,3]dioxol-5-yl)butanoate | (a3ii) |
| (a4i) | 5-chloro-8-(3-(propylamino)propyl)naphtho[1,2-d][1,3]dioxol-9-ol | (a4i) |
| (a5i) | 2-(benzo[d][1,3]dioxol-5-yl)acetonitrile | (a5i) |

TABLE 1-continued

List of names of isolated intermediates and other compounds:

| Compound abbreviation | Chemical name | Chemical structure |
|---|---|---|
| (a6i) | 2-(6-chlorobenzo[d][1,3]dioxol-5-yl)acetonitrile | (a6i) |
| (I) | (4aR,10aR)-1-propyl-1,2,3,4,4a,5,10,10a-octahydro-benzo[g]quinoline-6,7-diol | 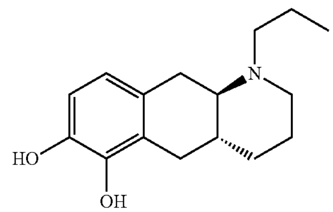 [SMILES: CCCN1CCC[C@@H]2Cc3c(ccc(O)c3O)C[C@H]21] |
| (Ib) | (6aR,10aR)-7-propyl-6,6a,7,8,9,10,10a,11-octahydro-[1,3]dioxolo[4',5':5,6]benzo[1,2-g]quinoline | 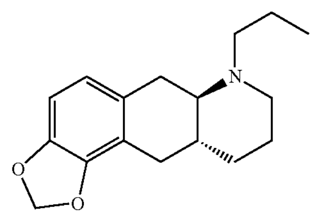 [SMILES: CCCN1CCC[C@@H]2Cc3c(ccc4c3OCO4)C[C@H]21] |

Step 0)

In step 0) an enamine intermediate compound (a2i) is formed. The intermediate compound a2i can be formed using two alternative steps, having different starting compounds:

Step 0 substep (i), wherein the keto ester (tert-butyl 4-(6-chlorobenzo[d][1,3]dioxol-5-yl)-3-oxobutanoate) compound (A1) is transformed to an enamine intermediate compound (a2i), with 3-chloropropan-1-amine in situ using catalytic amounts of zinc chloride.

Step 0 substep S1, is an alternative to substep (i) above, wherein compound (a6i) is subjected to the Blaise reaction with tert-butyl 2-bromoacetate and zinc, and then treated with acetic acid followed by 3-chloropropan-1-amine hydrochloride to obtain compound (a2i). In substep S1, compound (a2i) is formed directly and conveniently from compound (a6i).

In one embodiment of the invention, substep S1 comprises the isolation of compound (a2i).

Commercially available compound (a5i) can be chlorinated with $SO_2Cl_2$ to afford compound (a6i) in high yield. Thus, in a specific embodiment of the invention, compound (a5i) is chlorinated with $SO_2Cl_2$ to afford compound (a6i). In an even more specific embodiment of the invention, compound (a5i) is chlorinated with $SO_2Cl_2$ to afford compound (a6i), and step 0 substep S1 is subsequently used to afford compound (a2i).

Step 0' provides an alternative route to the starting material compound (A1) from compound (a6i):

The commercially available compound (a5i) can be chlorinated with $SO_2Cl_2$ to afford compound (a6i) in high yield. Compound (a6i) can subsequently be transformed into either compound (A1) or (a2i) depending on the reaction conditions.

To form compound (A1), compound (a6i) is subjected to the Blaise reaction with tert-butyl 2-bromoacetate and zinc and yields after aqueous acidic hydrolysis compound (A1).

In one embodiment of the invention, step 0' is used to obtain compound (A1) followed by step 0 substep (i) to form compound (a2i).

Step 1)

In step 1), compound (a2i) is transformed into desired enantiomer compound (A2) or compound (A2-hemi-L-tartate) by two alternative pathways.

In general, the presence of primary alkyl chloride and amine functionalities in the same molecule is expected to promote alkylation of the amine, which in the present case would lead to formation of azetidines. However, surprisingly, compounds (a2ii) and (A2) were found to have good stability despite the presence of primary alkyl chloride and amine functionalities in the same molecule, as they do not easily form the corresponding azetidines (a3i) or (a3ii), respectively (see below), or self-condense.

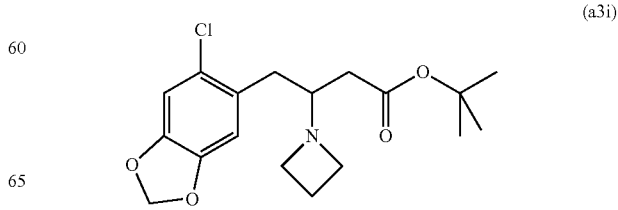

(a3i)

-continued

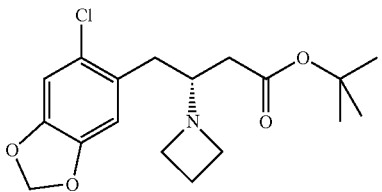
(a3ii)

Step 1, substep (ii) followed by substep (iii):

Further, the inventors have surprisingly found that the crude compound (a2ii) can, in substep (iii), be resolved via diastereomeric salt formation in high yield using L-tartaric acid in a solvent, for example a solvent selected from MeOH, EtOH and aqueous mixtures thereof, to afford the resolved amine (A2) as a hemi-L-tartrate salt (A2-hemi-L-tartrate) in a high enantiomeric excess above 95% (such as >99.5%) while also resulting in a high yield. Thus, in one embodiment of the invention, substep (ii) is used to obtain compound (a2i), and compound (a2i) is subsequently used in substep (iii) to afford (A2-hemi-L-tartrate).

In substep (ii), the enamine intermediate (a2i) is reduced with the use of for example sodium cyanoborohydride (NaBH$_3$CN), sodium triacetoxyborohydride (STAB), 5-ethyl-2-methylpyridine borane (PEMB) or NaBH$_4$ to afford crude (a2ii). In a specific embodiment of the invention, substep (ii) is performed using sodium cyanoborohydride.

Alternatively, in step 1 substep (ii), the reduction of compound (a2i) to compound (a2ii) can be performed with a platinum catalyst (preferably platinum on carbon) in the presence of hydrogen in a suitable solvent, e.g. Me-THF.

In one embodiment of the invention, substep (ii) is performed using a platinum catalyst at a temperature of about 20° C. to about 100° C., such as about 50° C. to about 80° C., such as about 55° C. to about 65° C., such as about 57° C., or about 58° C., or about 59° C., or about 60° C., or about 61° C., or about 62° C. or about 63° C.

In one embodiment of the invention, substep (ii) is performed using a platinum catalyst at a pressure of about 2 to about 10 bar, such as about 2 bar to about 6 bar, such as about 3 bar to about 5 bar, such as about 4 bar.

In one embodiment of the invention, substep (ii) is performed using a platinum catalyst at a temperature of about 50° C. to about 80° C. and a pressure of about 2 bar to about 6 bar.

In a more specific embodiment of the invention, substep (ii) is performed using a platinum catalyst at a temperature of about 60° C. and a pressure of about 4 bar.

In one embodiment of the invention, compound (a2i) as obtained from step 0 substep (i) above is subsequently reduced in the same pot with the use of for example NaBH$_3$CN, sodium triacetoxyborohydride (STAB), 5-ethyl-2-methylpyridine borane (PEMB) or NaBH$_4$ to afford crude (a2ii).

In substep (iii) compound (a2ii) is resolved using L-tartaric acid in a solvent, for example a solvent selected from MeOH, EtOH and aqueous mixtures thereof, to afford the resolved amine (A2) as a hemi-L-tartrate salt (A2-hemi-L-tartrate).

In one embodiment of the invention, compound (a2i) as obtained from step 0 substep (i) above is subsequently reduced in the same pot with the use of for example NaBH$_3$CN, sodium triacetoxyborohydride (STAB), 5-ethyl-2-methylpyridine borane (PEMB) or NaBH$_4$ to afford crude compound (a2ii), and the afforded crude compound (a2ii) is subsequently resolved in substep (iii) to obtain compound (A2-hemi-L-tartrate).

In an even more specific embodiment of the invention, compound (a2i) as obtained from step 0 substep (i) above is subsequently reduced in the same pot with the use of sodium cyanoborohydride to afford crude compound (a2ii), and the afforded crude compound (a2ii) is subsequently resolved in substep (iii) to obtain compound (A2-hemi-L-tartrate).

As an alternative to Step 1, substep (ii) followed by substep (iii) as described above, Step 1, Substep (iv) can be used to afford compound (A2):

The reduction of compound (a2i) to afford compound (A2), in Step 1 substep (iv), can be performed with a chiral catalyst, containing either rhodium, iridium or ruthenium, in the presence of hydrogen gas and a suitable solvent.

Specifically, the asymmetric hydrogenation of compound (a2i), in Step 1 substep (iv), can be carried out using a catalyst formed from Josiphos SL-J002-2 (cas #277306-29-3) and bis(2,5-norbornadiene)rhodium(I) tetrafluoroborate (cas #36620-11-8) in the presence of hydrogen and 2,2,2-trifluoroethanol as solvent to afford compound (A2) with 96% enantiomeric excess and 93% yield (based on LC-MS analysis).

In scheme 2 below is a more detailed overview of the substeps of step 0), and step 1).

Scheme 2: Detailed overview of substeps in step 0) and step 1)

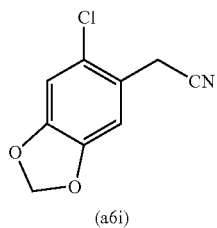

(a6i)

↓ (S1)

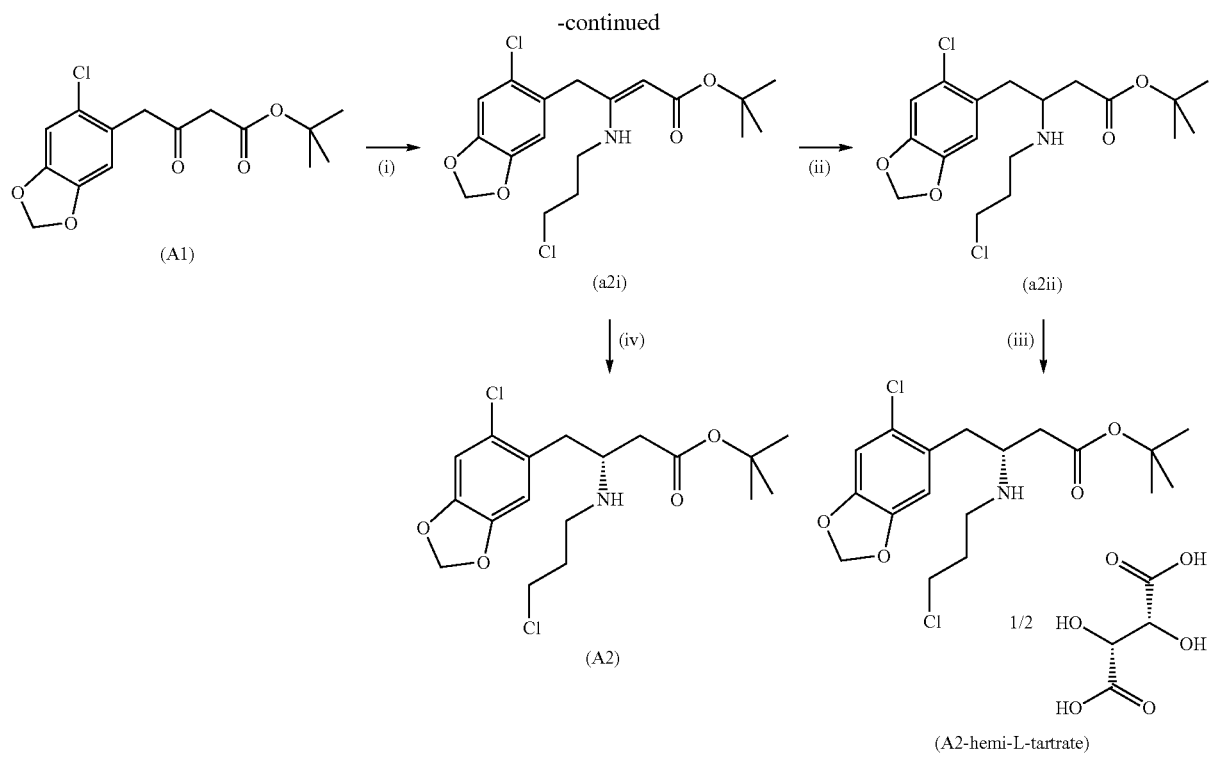

In one embodiment of the invention, Step 0 substep S1 is used to obtain compound (a2i) and is subsequently followed by Step 1.

In another more specific embodiment of the invention, step 0 substep S1 is followed by Step 1 substep (ii) and substep (iii) to obtain compound (A2-hemi-L-tartate).

In a more specific embodiment of the invention, Step 0 substep S1 is followed by Step 1 substep (iv) to obtain compound (A2).

In one embodiment of the invention, step 0' is used to obtain compound (A1).

Thus, in a more specific embodiment of the invention, step 0' is followed by step 0 substep (i) to obtain compound (a2i), and step 0 substep (i) is followed by step 1 substep (iv) to obtain compound (A2).

In a specific embodiment of the invention, step 0' is used to obtain compound (A1) and followed by step 0 substep (i) to obtain compound (a2i), step 0 substep (i) is subsequently followed by substep (ii) and substep (iii) to obtain compound (A2-hemi-L-tartate).

In another specific embodiment of the invention, step 0' is followed by step 0 substep (i) to obtain compound (a2i), and step 0 substep (i) is followed by step 1 substep (iv) to obtain compound (A2).

Step 2)

In step 2) as shown below in Scheme 3, compound (A2), or a salt thereof, undergoes a further reductive amination with propanal by using a reducing agent such as for example NaBH₃CN, sodium triacetoxyborohydride (STAB), borane 5-ethyl-2-methylpyridine borane (PEMB), or a platinum catalyst supported on a carrier such as carbon and hydrogen; in a solvent selected from for example tetrahydrofuran (THF), isopropanol (IPA) or MeOH; to provide compound (A3).

Scheme 3: Step 2)

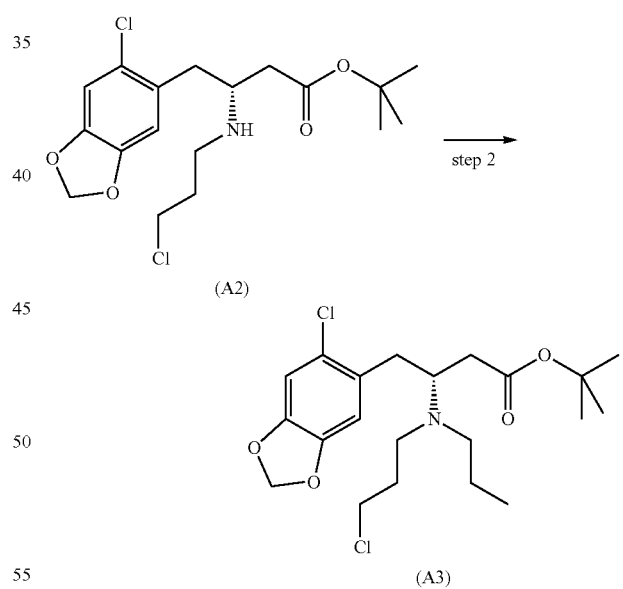

In a specific embodiment of the invention, compound (A2-hemi-L-tartate) is used in step 2 as described herein. Thus, in a more specific embodiment of the invention, Step 1 substep (ii) followed by Step 1 substep (iii) is used to obtain compound (A2-hemi-L-tartate), which is subsequently used in step 2.

In an even more specific embodiment of the invention, Step 0 substep S1 is followed by Step 1 substep (ii), which is followed by Step 1 substep (iii) to obtain compound (A2-hemi-L-tartate), which is subsequently used in step 2.

In a specific embodiment, sodium triacetoxyborohydride (STAB) is used as reducing agent in step 2.

In one embodiment of the invention, Step 2 is performed in a solvent selected from the group consisting of tetrahydrofuran (THF), isopropanol (IPA) and MeOH. In a more specific embodiment, Step 2 is performed in THF.

Step 3)

Step 3) as shown below in Scheme 4, provides a cyclisation of compound (A3) under basic conditions to yield compound (A4) which can optionally be isolated as a hemi-oxalate salt (A4-hemi-oxalate), a hydrogen chloride salt (A4-HCl) or a hydrogen bromide salt (A4-HBr).

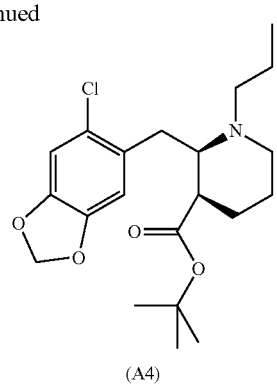

(A4)

In general, alkylation of esters has the drawback of by self-condensation (due to a Claisen reaction). Leaving groups, such as amines, in the beta position are expected to be eliminated readily leaving the acrylate system. However, the inventors found the cyclisation of compound (A3) to be surprisingly clean affording only little self-condensation products and/or elimination products, even though the reaction is run at the reasonable high temperature of −10° C. Typically, enolate formation from esters are run at cryogenic temperatures (e.g. −78° C.) to avoid side reactions, e.g. self-condensation (see for example Fan et al., Bioorg. Med. Chem. Lett. 2008, 18: 6236-6239 and Kotsuki et al., J. Org. Chem. 1992, 57: 5036-5040).

In one embodiment of the invention, compound (A4) is isolated as a hydrogen chloride salt compound (A4-HCl).

Surprisingly, the inventors have found that the compound (A4-HCl) can be precipitated as a powder with little or no clumping. These qualities further facilitate the process. Compound (A4-HCl) can be obtained by treatment of Compound (A4) with a solution of HCl.

Suitable solvents for the precipitation of a salt of compound (A4) may be one or more solvents selected from the group consisting of MeTHF, EtOAc, isopropanol, iPrOAc, acetone, toluene, heptane and mixtures thereof.

In a specific embodiment of the invention, a solvent selected from the group consisting of MeTHF, EtOAc, iPrOAc, acetone, toluene, a mixture of isopropanol (iPrOH) and heptane, a mixture of iPrOAc and heptane, and a mixture of acetone and heptane is used for precipitation of a salt of compound (A4), and even more specifically for precipitation of compound (A4-HCl).

In a specific embodiment of the invention, a solvent selected from the group consisting of MeTHF, a mixture of isopropanol (iPrOH) and heptane, a mixture of iPrOAc and heptane, and a mixture of acetone and heptane is used for precipitation of compound (A4-HCl).

In a more specific embodiment of the invention, a mixture of isopropanol and heptane is used for precipitation of compound (A4-HCl).

In a more specific embodiment of the invention, a mixture of acetone and heptane is used for precipitation of compound (A4-HCl).

When a salt of compound (A4), such as for example compound (A4-HCl) or compound (A4-hemi-oxalate) is isolated in the process of the invention, a base liberation may be used to liberate compound (A4) prior to initiating further synthesis steps, e.g. step 5. Thus, in one embodiment of the invention, a salt of compound (A4) is reacted with a suitable base, such as an aqueous solution of $Na_2CO_3$, $K_2CO_3$ or ammonia, to obtain a solution of compound (A4) as free base.

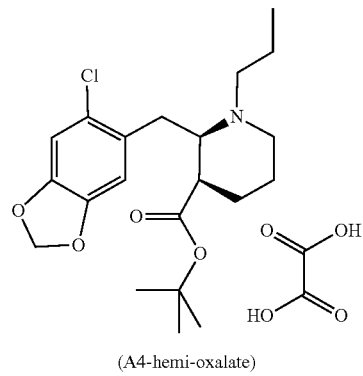

(A4-hemi-oxalate)

The reaction takes place in the presence of a strong base, preferably sodium bis(trimethylsilyl)amide (NaHMDS).

In one embodiment of the invention, step 3 is performed using a strong base selected from the group consisting of sodium bis(trimethylsilyl)amide (NaHMDS), lithium diisopropylamide (LDA), potassium bis(trimethylsilyl)amide (KHMDS) and lithium bis(trimethylsilyl)amide (LHMDS). In a specific embodiment of the invention, step 3 is performed using sodium bis(trimethylsilyl)amide (NaHMDS).

Suitable solvents for step 3 are for example a solvent selected from the group consisting of toluene, THF, and a mixture thereof. In a specific embodiment of the invention, a mixture of toluene and THF is used as a solvent.

Scheme 4: Step 3)

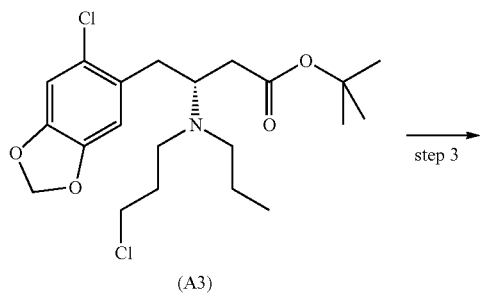

(A3) → step 3

In a specific embodiment of the invention, compound (A4-HCl) is reacted with a suitable base, such as am aqueous solution of Na$_2$CO$_3$, K$_2$CO$_3$ or ammonia to obtain a compound (A4) as free base.

Step 4)

In step 4) as shown in Scheme 5 below, an intramolecular Friedel-Craft acylation of compound (A4) yields the tricyclic compound (A5). The Friedel-Craft acylation is conveniently carried out using a mixture of P$_2$O$_5$ and TFA in chlorobenzene to convert compound (A4) to compound (A5).

Scheme 5: Step 4)

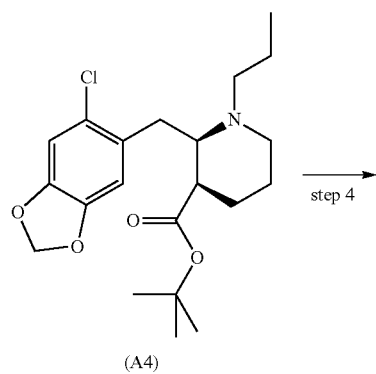

(A4)

The inventors found that compound (A5) is surprisingly stable under acidic conditions or as an acidic salt and can be conveniently isolated as a tosylate salt (see formula (A5-tosylate) below) in high yield following careful neutralization of the acidic reaction mixture.

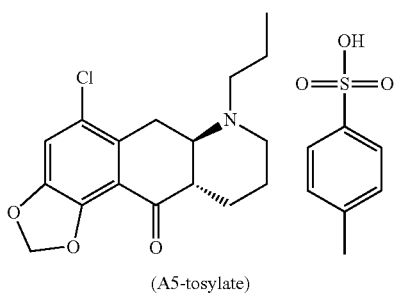

(A5-tosylate)

In contrast, if compound (A5) is isolated as the free base it slowly undergoes aromatization by elimination of the amine group to form compound (a4i), (see formula below), among other products. The formation of compound (a4i) from compound (A5) is not observed under acidic conditions, which is unexpected as under acidic conditions the nitrogen atom in compound (A5) is protonated and expected to be a better leaving group than under neutral or basic conditions.

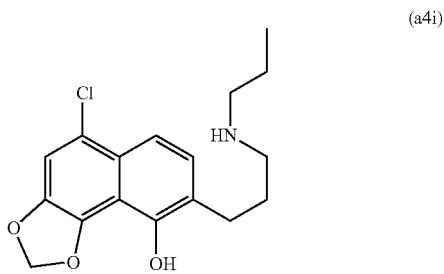 [SMILES: CCCNCCCc1ccc2c(Cl)cc3c(c2c1O)OCO3]

(a4i)

Thus, in one embodiment of the invention, Step 4 comprises the isolation of compound (A5) as an acid salt. In a more specific embodiment of the invention, Step 4 comprises the isolation of compound (A5-tosylate).

Step 5)

Step 5) as shown in Scheme 6 below, provides a one-pot hydrodechlorination and ketone reduction of compound (A5), or a salt thereof, in the presence of a palladium catalyst, such as Pd/C, and hydrogen to yield compound (Ib).

The high efficiency of the reaction is unexpected since contrary to the ketone-to-alkane reduction, which is promoted by acidic conditions, the hydrodechlorination reaction is generally impeded under acidic conditions, and instead promoted by basic conditions (Handbook of heterogeneous hydrogenation, S. Nishimura, Wiley 2001).

Scheme 6: Step 5)

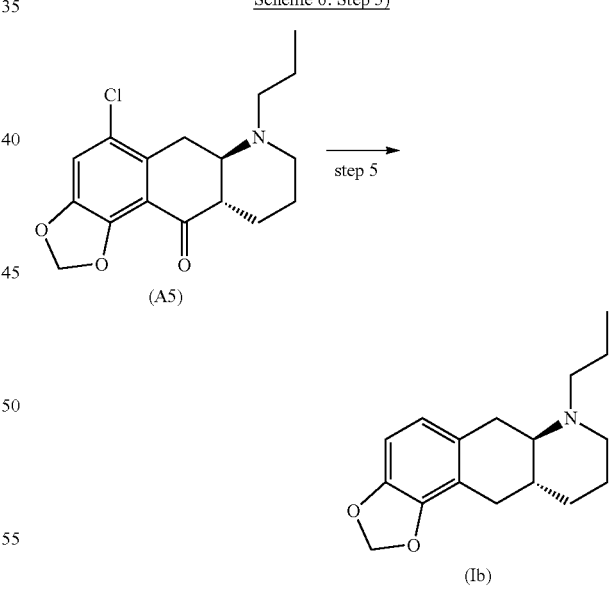

In one embodiment of the invention, compound (A5) or a salt thereof is used in step 5 to obtain compound (Ib). In another embodiment of the invention, compound (A5-tosylate) is used in step 5 to obtain compound (Ib).

Different solvents may be useful for the reaction in Step 5, in particular alcohol solvents. In one embodiment of the invention, an alcohol is used as a solvent in Step 5. In a more specific embodiment of the invention, Step 5 is performed using a solvent which is an alcohol selected from the group consisting of MeOH, EtOH, IPA and 1-propanol. In an even more specific embodiment, Step 5 is performed using EtOH as solvent.

The hydrogenation reaction in Step 5 may be performed using a palladium catalyst at a temperature ranging between about 20° C. to about 100° C., such as about 50° C. to about 100° C., such as about 60° C. to about 80° C., such as about 65° C., about 67° C., or about 68° C., about 69° C., about 70° C., about 71° C., about 72° C., about 73° C., about 75° C. or about 77° C.

The hydrogenation reaction in Step 5 may be performed using a palladium catalyst at a pressure ranging between about 2 bar to about 10 bar, such as about 3 bar to 6 bar, such as about 3 bar to about 5 bar, such as about 3.5 bar, or such as about 4 bar, or such as about 4.5 bar.

In a specific embodiment of the invention, Step 5 is performed using a palladium catalyst such as Pd/C, at a temperature of about 70° C. and a pressure of about 4 bar.

Step 6)

Finally, step 6) as shown in Scheme 7 below, provides a conversion of compound (Ib), or a salt thereof, to compound (I), or a salt thereof, by reaction of compound (Ib) with a Lewis acid or Brøndsted acid selected from the group consisting of BCl₃, BBr₃ and HBr.

Scheme 7: Step 6)

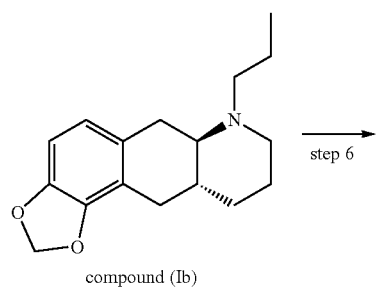

compound (Ib)

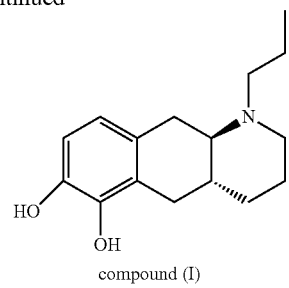

compound (I)

In a specific embodiment of the invention, step 6 comprises reacting compound (Ib) with BCl₃ to obtain compound (I) or a salt thereof.

In another specific embodiment of the invention, step 6 comprises reacting compound (Ib) as free base with BCl₃ to obtain compound (I) or a salt thereof.

When a salt of compound (Ib), such as for example compound (Ib-L-DTTA) is used as a starting material for Step 6, a base liberation may be used to liberate compound (Ib) prior to initiating further synthesis steps, e.g. step 6. Thus, in one embodiment of the invention, a salt of compound (Ib) is reacted with a base, such as an aqueous solution of Na₂CO₃, K₂CO₃ or ammonia, to obtain compound (Ib) as free base.

In a specific embodiment of the invention, compound (Ib-L-DTTA) is reacted with a suitable base, such as an aqueous solution of Na₂CO₃, K₂CO₃ or ammonia to obtain a compound (Ib) as free base.

In an even more specific embodiment of the invention, step 6 comprises reacting the (−)-O,O'-di-p-toluoyl-L-tartaric acid salt (L-DTTA) salt of compound (Ib), with an aqueous solution of Na₂CO₃, K₂CO₃ or ammonia to obtain a compound (Ib) as free base, followed by reacting compound (Ib) with BCl₃ to obtain compound (I) or a salt thereof, such as e.g. a HCl salt of compound (I).

Alternative Route for Obtaining Compound (I)

The inventors also developed an alternative process going from compound (A6) or compound (A6-tosylate) to enantiopure compound (Ib) in a three step process wherein compound (Ib) may be obtained as the L-DTTA salt ((−)-O,O'-di-p-toluoyl-L-tartaric acid salt), as illustrated in Scheme 8 below.

Scheme 8: Alternative route for obtaining compound (I)

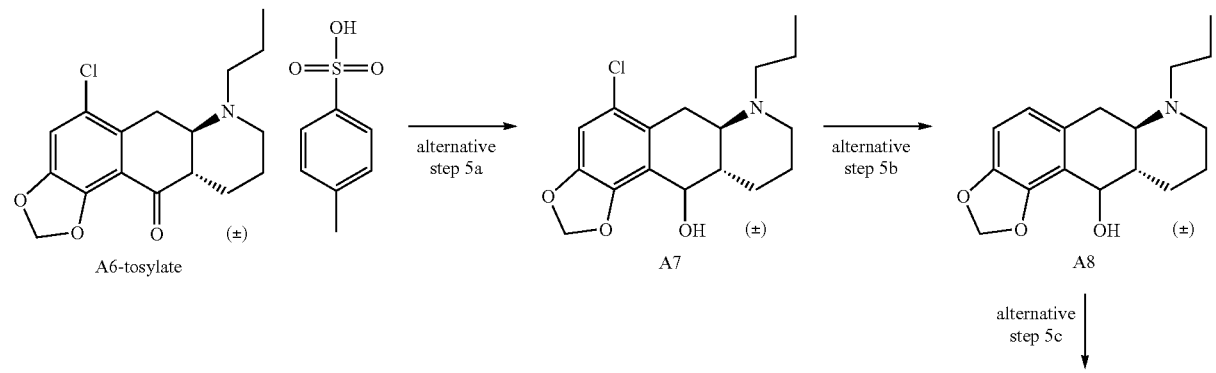

-continued

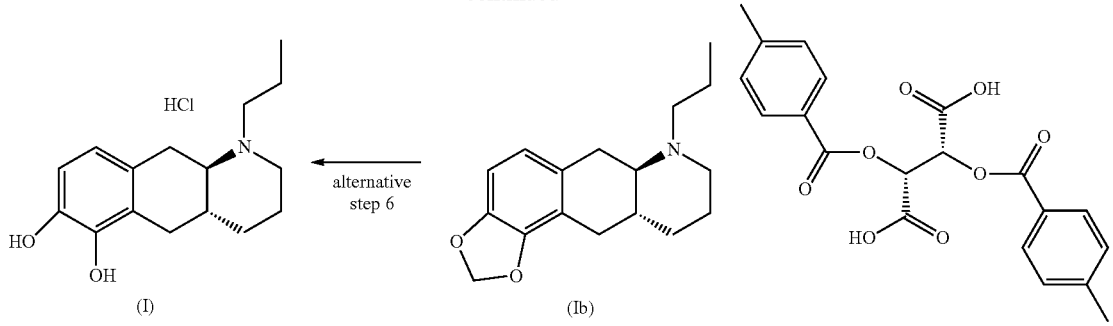

Alternative Step 5a)

In alternative step 5a) in the Scheme 8 above, compound (A6-tosylate) is converted to the free base with aqueous NaOH in Me-THF, and then reduced by addition of an aqueous solution of NaBH$_4$ to free base compound (A6) in Me-THF in 85% yield. The obtained compound (A7) is further reduced to compound (A8) in 90% yield in step 2, by transfer hydrogenation, where the reduction is facilitated by a Pd/C catalyst and formic acid, in an ammonium formate-MeOH-water mixture. Compound (A8) is transformed into compound (Ib-L-DTTA salt) in step 3, by first subjecting it to a hydrogenation with a Pd/C catalyst and hydrogen gas with added TsOH in IPA, followed by a classical resolution with L-DTTA in MeOH to yield compound (Ib-L-DTTA) with >99% enantiomeric excess.

Alternative Step 6)

Finally, in alternative step 6), compound (Ib-L-DTTA) is turned into the free base of compound (Ib) and the protection of the 1,2-dihydroxy moiety is removed with BCl$_3$ to afford after workup the HCl-salt of compound (I).

Contrary to this alternative process (comprising alternative step 5a, alternative step 5b and alternative 6 as shown in Scheme 8), the process comprising steps 5 and 6 of the invention (shown in Scheme 6 and 7) provides a more convenient and efficient process, since 1) resolution via diastereomeric salt formation is done at an earlier stage on compound (a2ii) compared to the late stage resolution of compound (Ib), and 2) the hydrodechlorination and ketone reduction is carried out in a single step, from compound (A5) to compound (Ib).

Embodiments of the Invention

In the following section, further embodiments of the invention are disclosed. The first embodiment is denoted E1, the second embodiment is denoted E2 and so forth.

E1. A process for the manufacture of compound (I) with the formula below

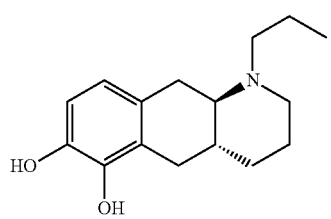

from the compound (Ib) with the formula below

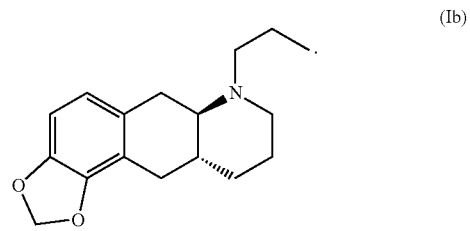 [SMILES: CCCN1CCC[C@@H]2Cc3c(ccc4c3OCO4)C[C@H]21]

E2. The process according to embodiment E1, wherein compound (Ib) is prepared by a process comprising the steps of:

Step 0)

Substep (i) reacting compound (A1) with 3-chloropropan-1-amine to obtain compound (a2i); or Substep (S1) reacting compound (a6i) with tert-butyl 2-bromoacetate and zinc to form a mixture, followed by treating the mixture from substep (S1) with acetic acid, followed by reacting said mixture with 3-chloropropan-1-amine hydrochloride to afford compound (a2i);

followed by

Step 1)

Substep (ii) reducing the compound (a2i) obtained in substep (i) or substep (S1) to obtain compound (a2ii), followed by Substep (iii) resolving compound (a2ii) using L-tartaric acid to afford compound (A2-hemi-L-tartrate); or Substep (i) or substep (S1) is followed by substep (iv) comprising the step of subjecting compound (a2i) as obtained in to a hydrogenation performed with a chiral catalyst in the presence of hydrogen and a solvent to afford compound (A2);

according to the reaction scheme below:

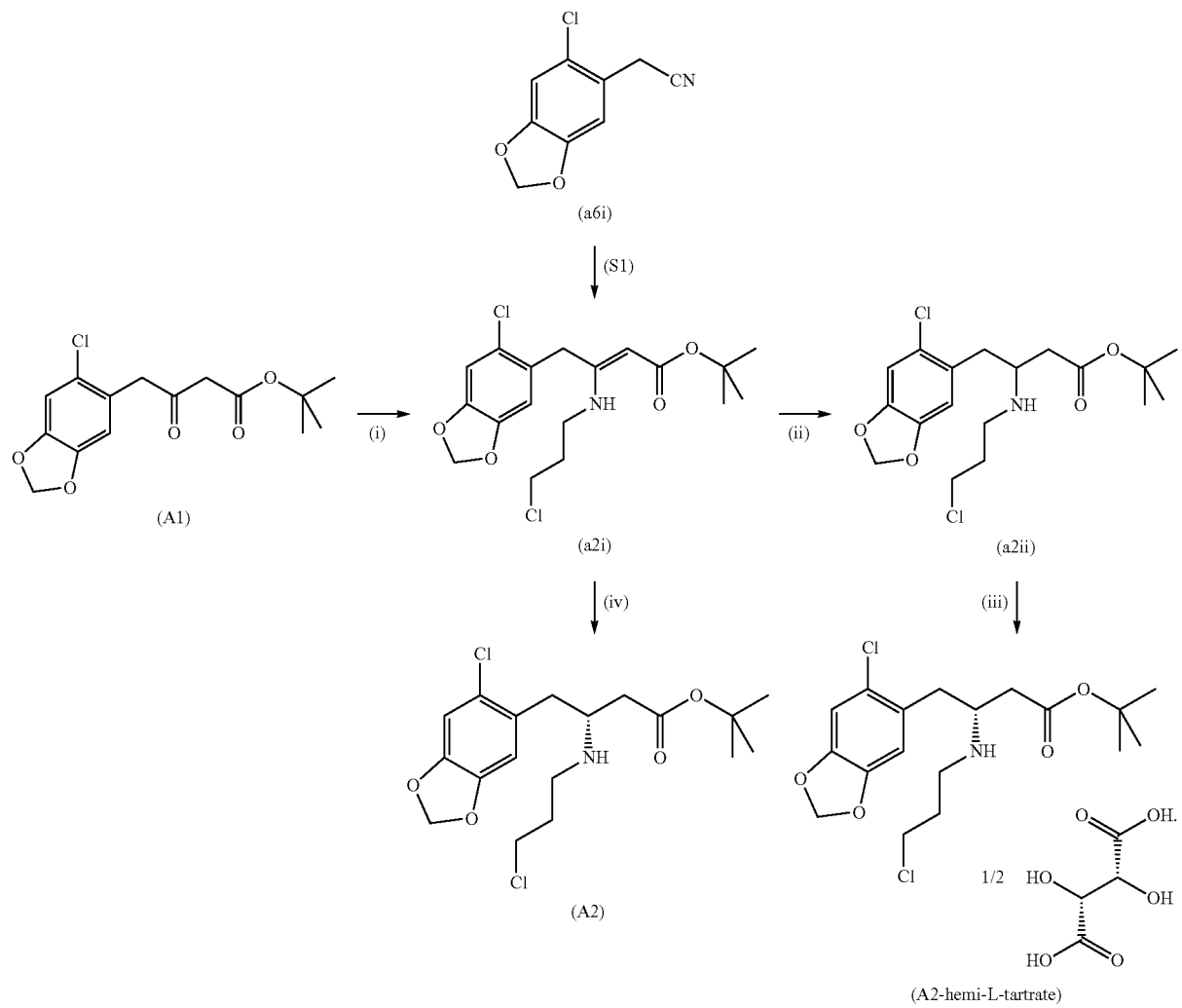

E3. The process according to embodiment E2, wherein the compound (a6i), or a salt thereof is prepared by a process comprising the step of reacting compound (a5i), or a salt thereof with a chlorinating agent

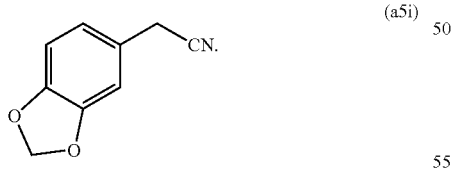

E4. The process according to embodiment E3, wherein the chlorinating agent is sulfuryl chloride.

E5. The process according to any one of embodiments E2 to E4, wherein the reduction in Step 1 substep (ii) takes place in the presence of a reducing agent.

E6. The process according to any one of embodiments E2 to E5, wherein the reducing agent selected from $NaBH_3CN$, sodium triacetoxyborohydride (STAB), a borane such as 5-ethyl-2-methylpyridine borane (PEMB) and $NaBH_4$.

E7. The process according to any one embodiments E2 to E6, wherein the reduction in Step 1 substep (ii) takes place by use of a platinum catalyst, preferably platinum on carbon.

E8. The process according to embodiment E1 to E4, wherein the chiral catalyst in Step 1 substep (iv) is selected from (2S)-1-[(1S)-1-[bis(1,1-dimethylethyl)phosphino]ethyl]-2-(diphenylphosphino)ferrocene and bis(2,5-norbornadiene)rhodium(I) tetrafluoroborate.

E9. The process according to claim E1 to E4 and E8, wherein the solvent in Step 1 substep (iv) is 2,2,2-trifluoroethanol.

E10. The compound of formula (A2) below or a salt thereof.

E11. The compound of embodiment E10 which is in the form of a hemi-L-tartrate salt as depicted below

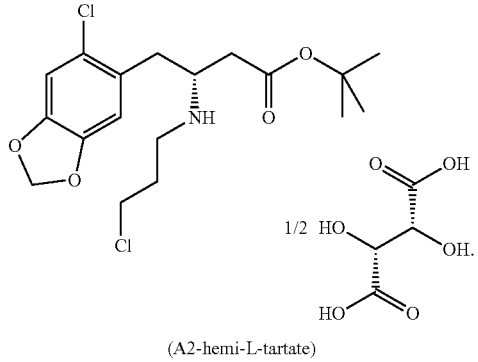

(A2-hemi-L-tartate)

E12. Use of a compound according to any of embodiments E10 and E11 in a process for the preparation of the compound of formula (I) or the compound of formula (Ib).

E13. The process according to any one of embodiments E1 to E9, wherein compound (Ib) is prepared by a process comprising the following step 2) reacting compound (A2) or compound (A2-hemi-L-tartrate) with propanal in the presence of a reducing agent, to afford compound (A3) according to reaction scheme a) or b) below scheme a)

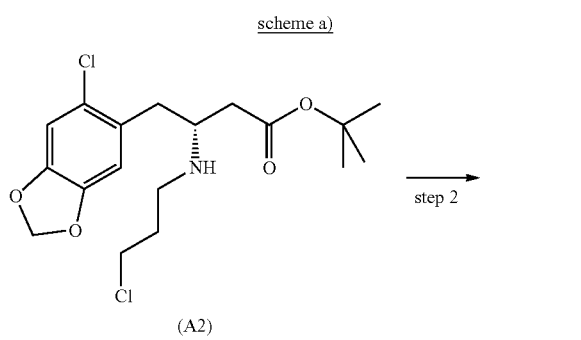

scheme b)

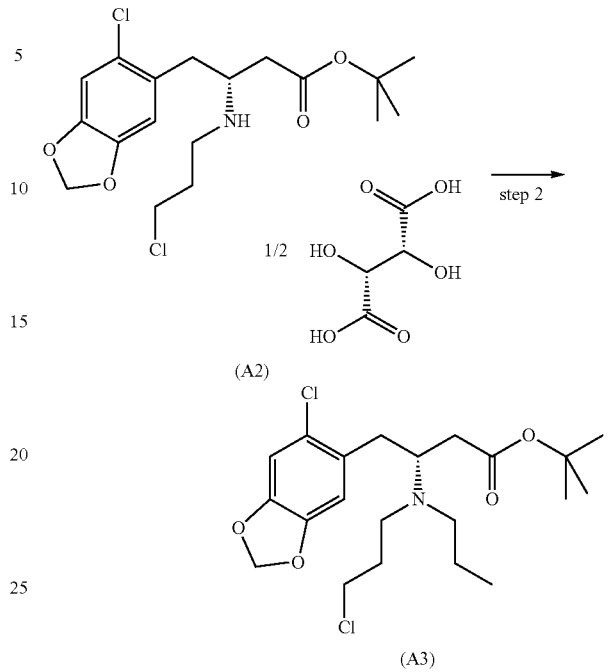

E14. The process according to embodiment E13, wherein compound (A3) is prepared by reacting compound (A2-hemi-L-tartrate) with propanal in the presence of a reducing agent.

E15. The process according to embodiment E14, wherein said reducing agent is selected from the group consisting of NaBH$_3$CN, sodium triacetoxyborohydride (STAB), a borane such as 5-ethyl-2-methylpyridine borane (PEMB), and a platinum catalyst, preferably platinum on carbon, with hydrogen gas.

E16. The process according to any of embodiments E13 to E15, wherein said reaction takes place in a solvent selected from example tetrahydrofuran (THF), isopropanol (IPA) or MeOH.

E17. The compound of formula (A3) below

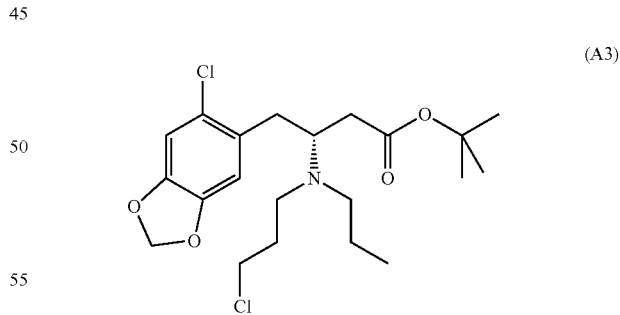

or a salt thereof.

E18. Use of a compound according to embodiment E17 in a process for the preparation of the compound of formula (I) or the compound of formula (Ib).

E19. The process according to embodiment E1 to E9, and E13 to E16, wherein compound (Ib) is prepared by a process comprising the following step 3) reacting compound (A3) with a strong base, to afford compound (A4) according to the reaction scheme below

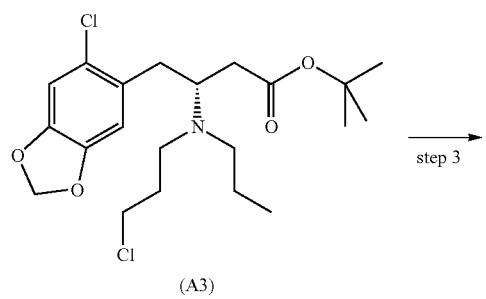

(A3)

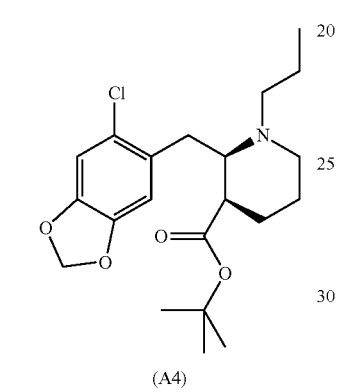

(A4)

optionally followed by isolating compound (A4) as a hemi-oxalate salt as depicted below

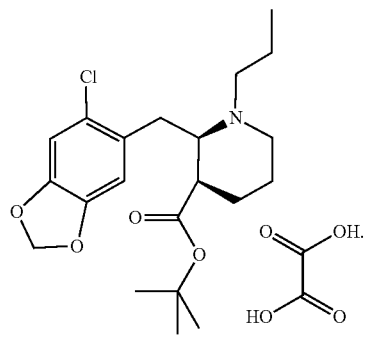

(A4-hemi-oxalate)

E20. The process according to embodiment E19, wherein said strong base is sodium bis(trimethylsilyl)amide (NaHMDS).

E21. The process according to any of embodiments E19 to E20, wherein said reaction between compound (A3) and base takes place at a temperature in the range of −20 to −5° C., such as in the range of −15 to −5° C. or such as at a temperature of about −10° C.

E22. The process according to any of embodiments E19 to E21, wherein said compound (A4) is mixed with oxalic acid and isolated as a hemi-oxalate salt.

E23. The compound of formula (A4) below

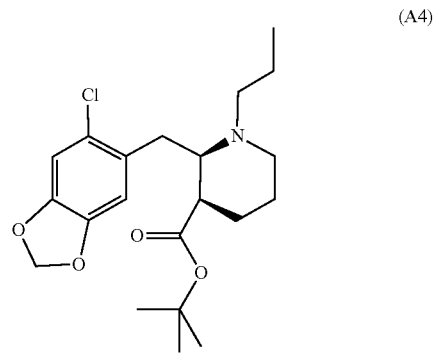 [SMILES: CCCN1CCC[C@@H](C(=O)OC(C)(C)C)[C@H]1Cc1cc2c(cc1Cl)OCO2]

or a salt thereof.

E24. The compound of embodiment E23 which is in the form of a hemi-oxalate salt as depicted below

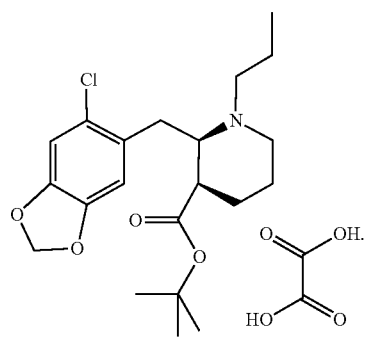

(A4-hemi-oxalate)

E25. Use of a compound according to any of embodiments E23 to E24 for in a process for the preparation of the compound of formula (I) or the compound of formula (Ib).

E26. The process according to embodiment E1 to E9, E13 to E16, E19 to E22, wherein compound (Ib) is prepared by a process comprising the following step 4) performing an intramolecular Friedel-Craft acylation of compound (A4) to afford compound (A5) according to the reaction scheme below

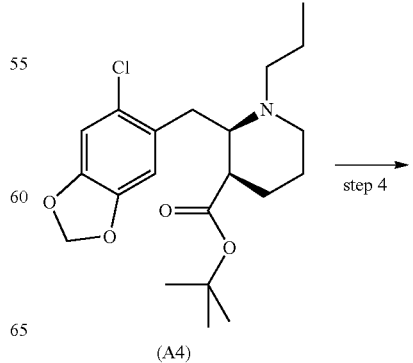

(A4)

-continued

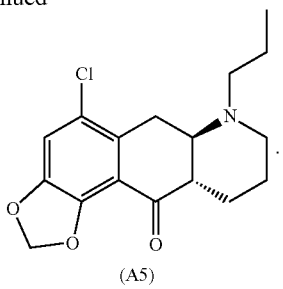

(A5)

optionally followed by isolating compound (A5) as a tosylate salt (A5-tosylate)

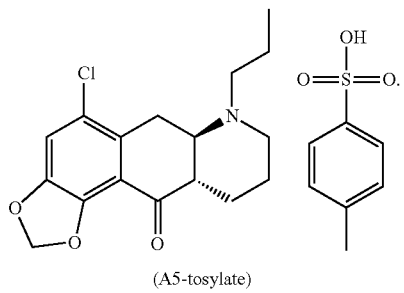

(A5-tosylate)

E27. The compound of formula (A5) below

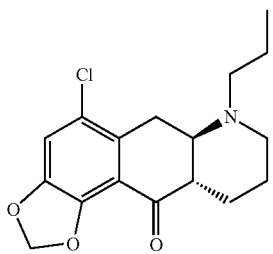

(A5)

or a salt thereof.

E28. The compound of embodiment E27 which is in the form of a tosylate salt as depicted below (A5-tosylate)

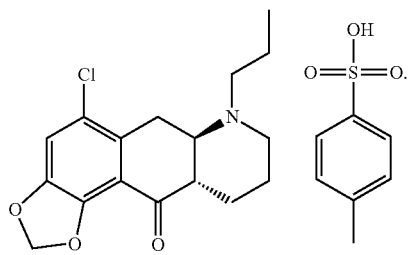

E29. Use of a compound according to any of embodiments E27 to E28 in a process for the preparation of the compound of formula (I) or the compound of formula (Ib).

E30. The process according to embodiment E1 to E9, E13 to E16, E19 to E22, and E26, wherein compound (Ib) is prepared by a process comprising the following step 5) reducing compound (A5), or a salt thereof, to obtain compound (Ib), or a salt thereof according to the reaction scheme below

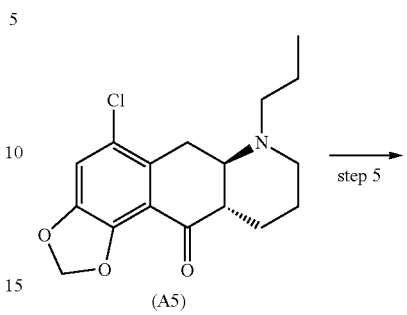

E31. The process according to embodiment E30, wherein said reduction takes place by use of a palladium catalyst.

E32. The process according to embodiment E1, wherein compound (Ib) is prepared by a process comprising the following steps Step 0) according to any one of embodiments E2 to E4
step 1) according to any of embodiments E2 and E5 to E9; followed by
step 2) according to any of embodiments E13 to E16.

E33. The process according to any one of embodiments E1 to E7, wherein compound (Ib) is prepared by a process comprising the following steps
step 2) according to any of embodiments E13 to E16; followed by
step 3) according to any of embodiments E19 to E22.

E34. The process according to any one of embodiments E1 to E7, and E11 to E13, wherein compound (Ib) is prepared by a process comprising the following steps
step 3) according to any of embodiments E19 to E22; followed by
step 4) according to embodiment E26.

E35. The process according to any one of the embodiments E1 to E7, wherein compound (Ib) is prepared by a process comprising the following steps
step 4) according to any one of embodiments E26; followed by
step 5) according to embodiments E30 to E31.

E36. The process according to embodiment 1, wherein compound (Ib) is prepared by a process comprising the following steps
step 0) according to any one of embodiments E2 to E4
step 1) according to any of embodiments E2 and E5 to E9; followed by
step 2) according to any of embodiments E13 to E16; followed by
step 3) according to any of embodiments E19 to E22.

E37. The process according to embodiment 1, wherein compound (Ib) is prepared by a process comprising the following steps step 2) according to any of embodiments E13 to E16; followed by
step 3) according to any of embodiments E19 to E22; followed by
step 4) according to embodiment E26.

E38. The process according to embodiment 1, wherein compound (Ib) is prepared by a process comprising the following steps
step 3) according to any of embodiments E19 to E22; followed by
step 4) according to embodiment E26; followed by
step 5) according to any of embodiments E30 to E31.

E39. The process according to embodiment 1, wherein compound (Ib) is prepared by a process comprising the following steps
step 0) according to any one of embodiments E2 to E4; followed by
step 1) according to any of embodiments E2 and E5 to E9; followed by
step 2) according to any of embodiments E13 to E16; followed by
step 3) according to any of embodiments E19 to E22; followed by
step 4) according to embodiment E26.

E40. The process according to embodiment 1, wherein compound (Ib) is prepared by a process comprising the following steps
step 2) according to any of embodiments E13 to E16; followed by
step 3) according to any of embodiments E19 to E22; followed by
step 4) according to embodiment E26; followed by
step 5) according to any of embodiments E30 to E31.

E41. The process according to embodiment 1, wherein compound (Ib) is prepared by a process comprising the following steps
step 0) according to any one of embodiments E2 to E4; followed by
step 1) according to any of embodiments E2 and E5 to E9; followed by
step 2) according to any of embodiments E13 to E16; followed by
step 3) according to any of embodiments E19 to E22; followed by
step 4) according to embodiment E26; followed by
step 5) according to any of embodiments E30 to E31.

E42. The process for the manufacture of compound (I) according to any of embodiments E1-E9, E13-E16, E19-E22, E26, and E30 to E31, wherein compound (I) is prepared from compound (Ib) by the following step
6) reacting compound (Ib) with a Lewis acid or Brønsted acid selected from the group consisting of BCl$_3$, BBr$_3$ and HBr,
to obtain compound (I) according to the reaction scheme below

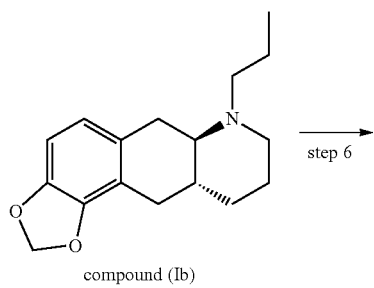

compound (Ib)

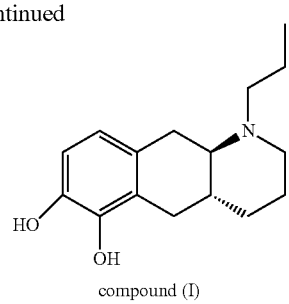

compound (I)

E43. The process according to embodiment E42, wherein step 6) follows after step 5).

E44. The process for the manufacture of compound (I) according to any of embodiments, E35, E38, and E40 to E42, wherein step 5) is followed by step 6).

E45. The process for the manufacture of compound (I) according to any one of the embodiments E1 to E9, E13 to E16, E19 to E22, E26, and E30 to E31, wherein the process is a chemical process ex vivo.

E46. A compound of formula (a2i) below

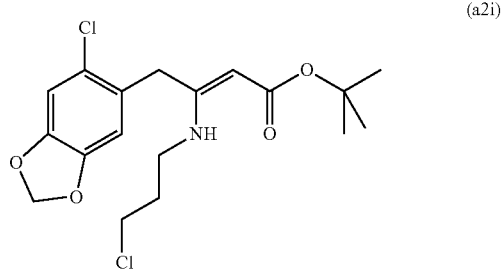 [SMILES: CC(C)(C)OC(=O)/C=C(/Cc1cc2c(cc1Cl)OCO2)NCCCCl]

or a salt thereof.

E47. A compound of formula (a2ii) below

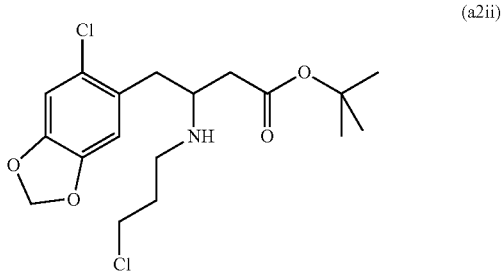 [SMILES: CC(C)(C)OC(=O)CC(Cc1cc2c(cc1Cl)OCO2)NCCCCl]

or a salt thereof.

E48. The process according to any one of embodiments E1-E9, E13-E16, E19-E22, E26 and E30-E45, wherein compound (a2i) is isolated.

E49. The process according to any one of embodiments E1-E6, E13-E16, E19-E22, E26 and E30-E45, and E48, wherein the reducing agent used in Step 1 substep (ii) is sodium cyanoborohydride.

E50. The process according to any one of embodiments E1-E5, E7, E13-E16, E19-E22, E26, E30-E45 and E48-E49, wherein Step 1 substep (ii) is performed using a platinum catalyst at a temperature of about 20° C. to about 100° C., such as about 50° C. to about 80° C., such as about 55° C.

to about 65° C., such as about 57° C., or about 58° C., or about 59° C., or about 60° C., or about 61° C., or about 62° C. or about 63° C.

E51. The process according to any one of embodiments E1-E5, E7, E13-E16, E19-E22, E26, E30-E45 and E48-E50, wherein Step 1 substep (ii) is performed using a platinum catalyst at a pressure of about 2 to about 10 bar, such as about 2 bar to about 6 bar, such as about 3 bar to about 5 bar, such as about 4 bar.

E52. The process according to any one of embodiments E1-E5, E7, E13-E16, E19-E22, E26, E30-E45 and E48-E51, wherein Step 1 substep (ii) is performed using a platinum catalyst at a temperature of about 50° C. to about 80° C. and a pressure of about 2 bar to about 6 bar.

E53. The process according to any one of embodiments E1-E5, E7, E13-E16, E19-E22, E26, E30-E45 and E48-E52, wherein Step 1 substep (ii) is performed using a platinum catalyst at a temperature of about 60° C. and a pressure of about 4 bar.

E54. The process according to any one of embodiments E1-E7, E13-E16, E19-E22, E26, E30-E45 and E48-E53, wherein Step 1 substep (iii) is performed using an alcohol as solvent, such as a solvent selected from MeOH, EtOH and aqueous mixtures thereof.

E55. The process according to any one of embodiments E13-E16, E19-E22, E26, E32-E33, E36-E37, E39-E45 and E48-E54, wherein the reducing agent used in Step 2 is selected from NaBH$_3$CN, sodium triacetoxyborohydride (STAB), a borane such as 5-ethyl-2-methylpyridine borane (PEMB), and a platinum catalyst, preferably platinum on carbon, with hydrogen gas.

E56. The process according to any one of embodiments E13-E16, E19-E22, E26, E32-E33, E36-E37, E39-E45 and E48-E55, wherein the reducing agent used in Step 2 is sodium triacetoxyborohydride (STAB).

E57. The process according to any one of embodiments E13-E16, E19-E22, E26, E32-E33, E36-E37, E39-E45 and E48-E56, wherein step 2 is performed in a solvent selected from the group consisting of tetrahydrofuran (THF), isopropanol (IPA) and MeOH.

E58. The process according to any one of embodiments E13-E16, E19-E22, E26, E32-E33, E36-E37, E39-E45 and E48-E57, wherein step 2 is performed in THF.

E59. The process according to any one of embodiments E19-E22, E26, E30-E31, E33-E34, E36-E45 and E48-E58, wherein step 3 is performed using a strong base selected from the group consisting of sodium bis(trimethylsilyl) amide (NaHMDS), lithium diisopropylamide (LDA), potassium bis(trimethylsilyl)amide (KHMDS) and lithium bis (trimethylsilyl)amide (LHMDS).

E60. The process according to any one of embodiments E19-E22, E26, E30-E31, E33-E34, E36-E45 and E48-E59, wherein Step 3 is performed using a solvent selected from the group consisting of toluene, THF, and a mixture thereof.

E61. The process according to any one of embodiments E19-E21, E26, E30-E31, E33-E34, E36-E45 and E48-E60, wherein Step 3 is followed by isolating compound (A4) as a salt selected from the group consisting of a hemi-oxalate salt compound (A4-hemi-oxalate), a hydrogen chloride salt compound (A4-HCl) or a hydrogen bromide salt compound (A4-HBr).

E62. The process according to any one of embodiments E19-E21, E26, E30-E31, E33-E34, E36-E45 and E48-E61, wherein Step 3 is followed by reacting compound (A4) with a solution of HCl and isolating the hydrogen chloride salt compound (A4-HCl).

E63. The process according to any one of E19-E22, E26, E30-E31, E33-E34, E36-E45 and E48-E62, wherein Step 3 is followed by isolating compound (A4) using a solvent selected from the group consisting of MeTHF, EtOAc, isopropanol, iPrOAc, acetone, toluene, heptane and mixtures thereof.

E64. The process according to any one of embodiments E19-E21, E26, E30-E31, E33-E34, E36-E45 and E48-E63, wherein Step 3 is followed by isolating compound (A4-HCl) using a mixture of isopropanol and heptane.

E65. The process according to any one of embodiments E19-E21, E26, E30-E31, E33-E34, E36-E45 and E48-E64, wherein Step 3 is followed by isolating compound (A4-HCl) using a mixture of acetone and heptane.

E66. The process according to any one of embodiments E19-E22, E26, E30-E31, E33-E34, E36-E45 and E48-E66, further comprising a step wherein an isolated salt of compound (A4) is reacted with a base, to obtain compound (A4) as a free base.

E67. The process according to any one of embodiments E19-E22, E26, E30-E31, E33-E34, E36-E45 and E48-E66, further comprising a step wherein a salt of compound (A4) is reacted with an aqueous solution of Na$_2$CO$_3$, K$_2$CO$_3$ or ammonia to obtain compound (A4) as a free base.

E68. The process according to any one of embodiments E19-E22, E26, E30-E31, E34-E35, E37-E45 and E48-E67, further comprising a step wherein compound (A4-HCl) is reacted with an aqueous solution of Na$_2$CO$_3$, K$_2$CO$_3$ or ammonia to obtain compound (A4) as a free base.

E69. The process according to any one of embodiments E26, E30-E31, E34-E35, E37-E45 and E48-E68, wherein Step 4 comprises the isolation of compound (A5) as an acid salt.

E70. The process according to any one of embodiments E26, E30-E31, E34-E35, E37-E45 and E48-E69, wherein the Friedel-Craft acylation in Step 4 is performed using a mixture of P$_2$O$_5$ and TFA in a suitable solvent, such as chlorobenzene.

E71. The process according to any one of embodiments E30-E31, E35, E38, E40-E45 and E48-E70, wherein compound (A5) or a salt thereof is used in Step 5 to obtain compound (Ib).

E72. The process according to any one of embodiments E30-E31, E35, E38, E40-E45 and E48-E71, wherein compound (A5-tosylate) is used in Step 5 to obtain compound (Ib).

E73. The process according to any one of embodiments E30-E31, E35, E38, E40-E45 and E48-E72, wherein an alcoholic solvent is used in Step 5.

E74. The process according to any one of embodiments E30-E31, E35, E38, E40-E45 and E48-E73, wherein a solvent selected from the group consisting of MeOH, EtOH, IPA and 1-propanol is used in step 5.

E75. The process according to any one of embodiments E30-E31, E35, E38, E40-E45 and E48-E74, wherein EtOH is used as a solvent in step 5.

E76. The process according to any one of embodiments E30-E31, E35, E38, E40-E45 and E48-E75, wherein the hydrogenation reaction in Step 5 is performed using a palladium catalyst at a temperature ranging between about 20° C. to about 100° C., such as about 50° C. to about 100° C., such as about 60° C. to about 80° C., such as about 65° C., about 67° C., or about 68° C., about 69° C., about 70° C., about 71° C., about 72° C., about 73° C., about 75° C. or about 77° C.

E77. The process according to any one of embodiments E30-E31, E35, E38, E40-E45 and E48-E76, wherein the hydrogenation reaction in Step 5 is performed using a palladium catalyst at a pressure ranging between about 2 bar to about 10 bar, such as about 3 bar to 6 bar, such as about 3 bar to about 5 bar, such as about 3.5 bar, or such as about 4 bar, or such as about 4.5 bar.

E78. The process according to any one of embodiments E42-E45 and E48-E77, wherein step 6 comprises reacting compound (Ib) with BCl₃ to obtain compound (I) or a salt thereof.

E79. The process according to any one of embodiments E42-E45 and E48-E78, wherein step 6 comprises reacting compound (Ib) as free base with BCl₃ to obtain compound (I) or a salt thereof.

E80. The process according to any one of embodiments E42-E45 and E48-E79, wherein step 6 comprises reacting a salt of compound (Ib) with a base to obtain compound (Ib) as free base, followed by reacting compound (Ib) with BCl₃ to obtain compound (I) or a salt thereof.

E81. The process according to any one of embodiments E42-E45 and E48-E80, wherein step 6 comprises reacting a salt of compound (Ib) with an aqueous solution of Na₂CO₃, K₂CO₃ or ammonia to obtain compound (Ib) as free base followed by reacting compound (Ib) with BCl₃ to obtain compound (I) or a salt thereof.

E82. The process according to any one of embodiments E42-E45 and E48-E81, wherein step 6 comprises reacting the (−)-O,O'-di-p-toluoyl-L-tartaric acid salt (L-DTTA) salt of compound (Ib), with a base to obtain the free base of compound (Ib) followed by reacting compound (Ib) with BCl₃ to obtain compound (I) or a salt thereof, such as a HCl salt of compound (I).

E83. The compound of embodiment E23, which is in the form of a hydrogen chloride salt as depicted below

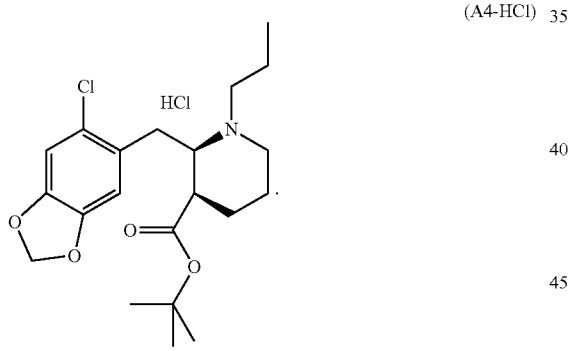

(A4-HCl)

E84. Use of a compound according to any of embodiments E23 and E83 in a process for the preparation of the compound of formula (I) or the compound of formula (Ib).

E85. A process for the manufacture of compound (I) with the formula below

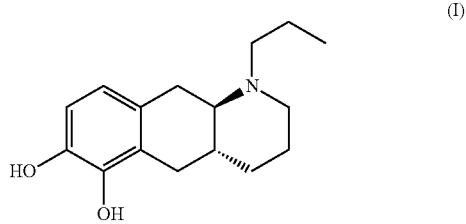 [SMILES: CCCN1CCC[C@@H]2Cc3c(ccc(O)c3O)C[C@H]21]

(I)

from the compound (Ib) with the formula below

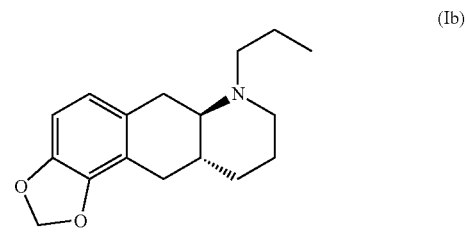 [SMILES: CCCN1CCC[C@@H]2Cc3c(ccc4c3OCO4)C[C@H]21]

(Ib)

wherein compound (Ib) is prepared by a process comprising the steps of:

Step 0)

Substep (S1) reacting compound (a6i) with tert-butyl 2-bromoacetate and zinc to form a mixture, followed by treating the mixture from substep (S1) with acetic acid, followed by reacting said mixture with 3-chloropropan-1-amine hydrochloride to afford compound (a2i);

followed by

Step 1)

Substep (ii) reducing the compound (a2i) obtained in substep (S1) to obtain compound (a2ii), followed by Substep (iii) resolving compound (a2ii) using L-tartaric acid to afford compound (A2-hemi-L-tartrate);

according to the reaction scheme below:

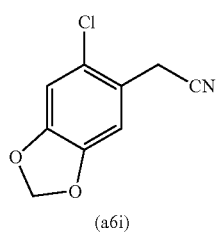

(a6i)

↓ (S1)

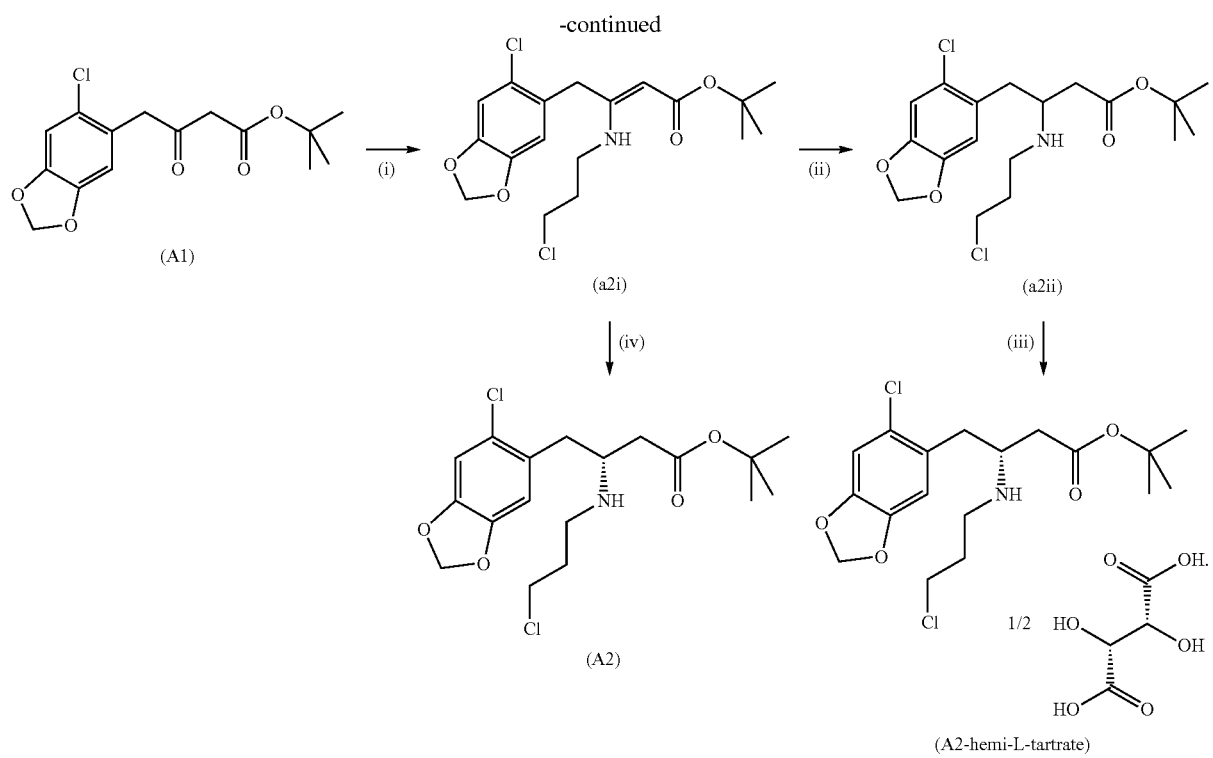

E86. The process according to embodiment E85, wherein the compound (a6i), or a salt thereof is prepared by a process comprising the step of reacting compound (a5i), or a salt thereof with a chlorinating agent

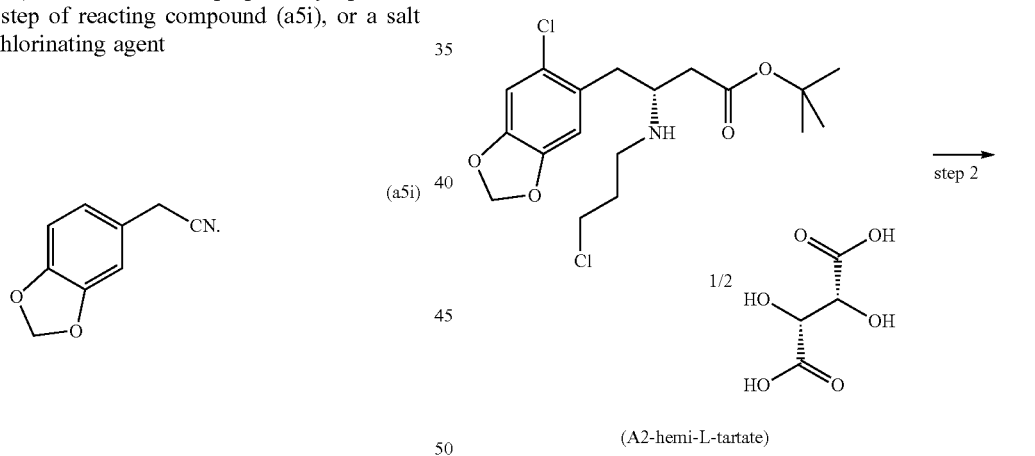

E87. The process according to embodiment E86, wherein the chlorinating agent is sulfuryl chloride.

E88. The process according to any one of embodiments E85-E87 wherein compound (a2i) is isolated prior to initiating Step 1 substep (ii).

E89. The process according to any one of embodiments E85-E88 further defined by any one of the embodiments E5-E7, E12-E16, E19-E22, E26, E30-E45, and E48-E82.

E90. The process according to any one of embodiments E85-E89, wherein compound (A3) is prepared by a process comprising the following step 2) reacting compound (A2-hemi-L-tartrate) with propanal in the presence of a reducing agent, to afford compound (A3) according to reaction scheme b) below All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only and should not be construed as limiting the invention in any way.

The description herein of any aspect or aspect of the invention using terms such as "comprising", "having," "including" or "containing" with reference to an element or elements is intended to provide support for a similar aspect or aspect of the invention that "consists of", "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (including "for instance", "for example", "e.g.", "such as" and "as such") in the present specification is intended merely to better illuminate the invention and does not pose a limitation on the scope of invention unless otherwise indicated.

It should be understood that the various aspects, embodiments, implementations and features of the invention mentioned herein may be claimed separately, or in any combination.

The present invention includes all modifications and equivalents of the subject-matter recited in the claims appended hereto, as permitted by applicable law.

Item List

In the following list of items, some further embodiments of the invention are disclosed. The first embodiment is denoted EE1, the second embodiment is denoted EE2 and so forth.

EE1. A process for the manufacture of compound (Ib) with the formula below

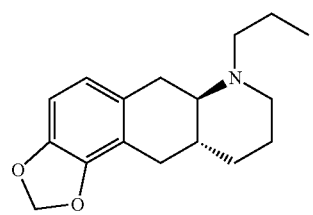

comprising the steps of:
Step 0)
Substep (i) reacting compound (A1) with 3-chloropropan-1-amine to obtain compound (a2i); or
Substep (S1) reacting compound (a6i) with tert-butyl 2-bromoacetate and zinc to form a mixture, followed by
treating the mixture from step (S1) with acetic acid, followed by reacting said mixture with 3-chloropropan-1-amine hydrochloride to afford compound (a2i);
followed by
Step 1)
Substep (ii) reducing the compound (a2i) obtained in step substep (i) or substep (S1) to obtain compound (a2ii), followed by
Substep (iii) resolving compound (a2ii) using L-tartaric acid to afford compound (A2-hemi-L-tartrate); or
Substep (i) or substep (S1) is followed by substep step (iv) comprising the step of subjecting compound (a2i) to a hydrogenation performed with a chiral catalyst in the presence of hydrogen and a solvent to afford compound (A2); according to the reaction scheme below:

Item List
In the following list of items, some further embodiments of the invention are disclosed. The first embodiment is denoted EE1, the second embodiment is denoted EE2 and so forth.

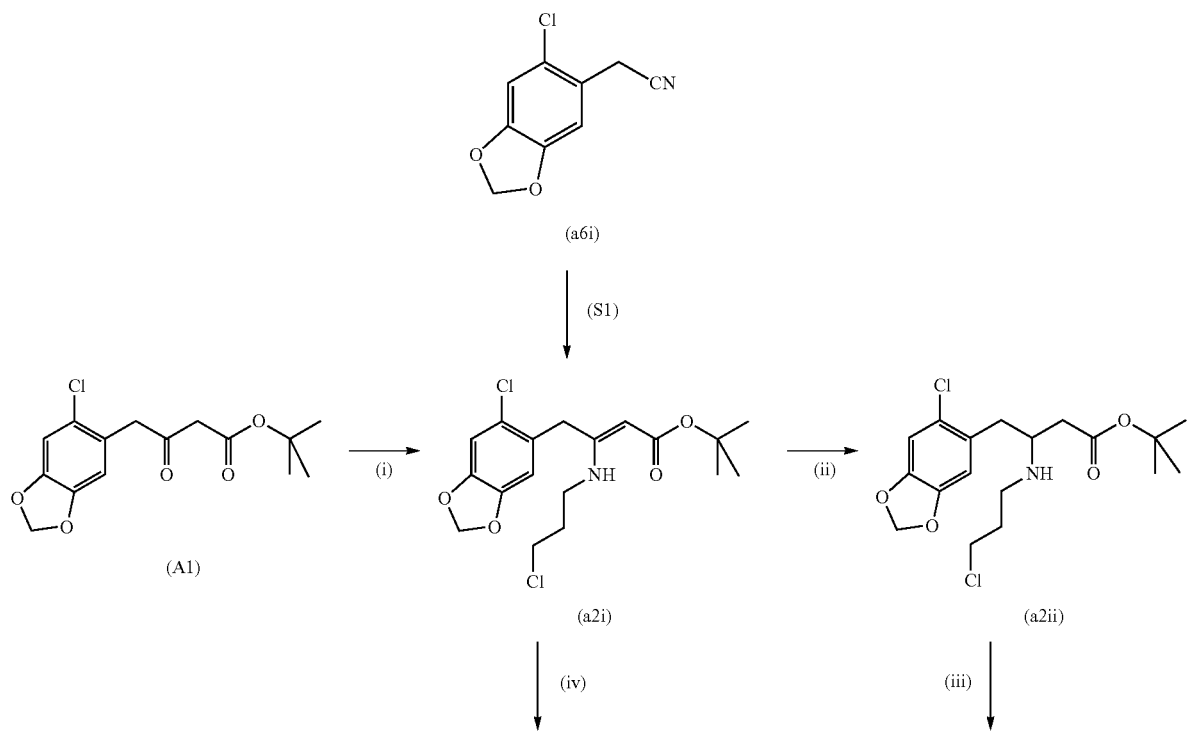

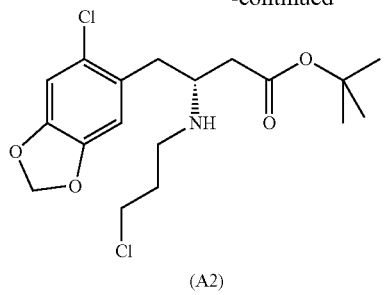

(A2)

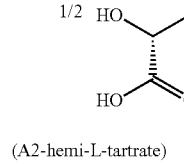

(a5i)

EE2. The process according to embodiment E1, wherein the compound (a6i) is prepared by a process comprising the step of reacting compound (a5i) with a chlorinating agent EE3. The process according to embodiment EE2, wherein the chlorinating agent is sulfuryl chloride.

EE4. The process according to any one of embodiments EE1 to EE3, wherein the reduction in Step 1 substep (ii) takes place in the presence of a reducing agent.

EE5. The process according to any one of embodiments EE1 to EE4, wherein the reducing agent selected from NaBH$_3$CN, sodium triacetoxyborohydride (STAB), a borane such as 5-ethyl-2-methylpyridine borane (PEMB) and NaBH$_4$.

EE6. The process according to any one embodiments EE1 to EE5, wherein the reduction in Step 1 substep (ii) takes place by use of a platinum catalyst, preferably platinum on carbon.

EE7. The process according to embodiment EE1 to EE3, wherein the chiral catalyst in Step 1 substep (iv) is selected from (2S)-1-[(1S)-1-[bis(1,1-dimethylethyl)phosphino]ethyl]-2-(diphenylphosphino)ferrocene and bis(2,5-norbornadiene)rhodium(I) tetrafluoroborate.

EE8. The process according to claim EE1 to EE3 and EE7, wherein the solvent in Step 1 substep (iv) is 2,2,2-trifluoroethanol.

(A2-hemi-L-tartrate)

EE9. The compound of formula (A2) below

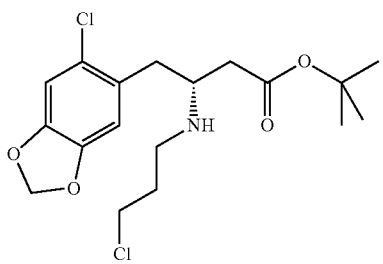

(a2)

or a salt thereof.

EE10. The compound of embodiment E8 which is in the form of a hemi-L-tartrate salt as depicted below

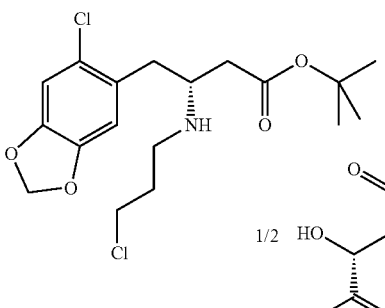

(A2-hemi-L-tartate)

EE11. Use of a compound according to any of embodiments EE9 and EE10 in a process for the preparation of the compound of formula (I) or the compound of formula (Ib).

EE12. The process according to any one of embodiments EE1 to EE8, wherein compound (Ib) is prepared by a process comprising the following step
2) reacting compound (A2) or compound (A2-hemi-L-tartrate) with propanal in the presence of a reducing agent,
to afford compound (A3) according to reaction scheme a) or b) below scheme a)

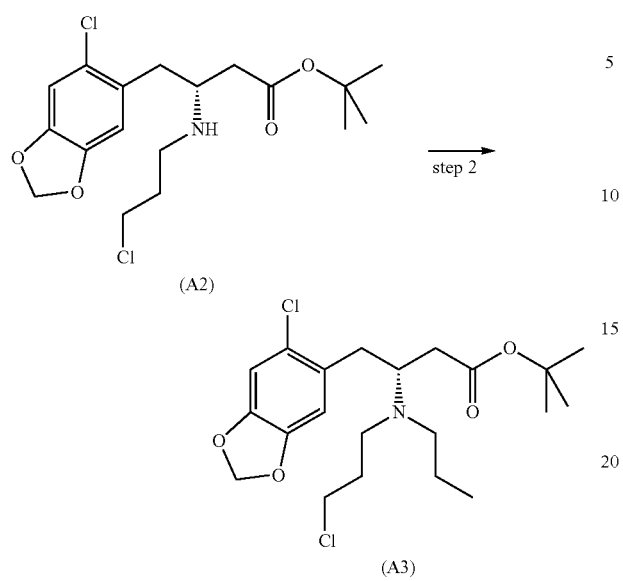

EE15. The process according to any of embodiments EE12 to EE14, wherein said reaction takes place in a solvent selected from example tetrahydrofuran (THF), isopropanol (IPA) or MeOH.

EE16. The compound of formula (A3) below

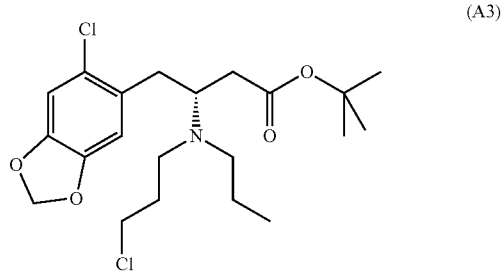 [SMILES: CCCN(CCCCl)[C@@H](CC(=O)OC(C)(C)C)Cc1cc2c(cc1Cl)OCO2]

or a salt thereof.

EE17. Use of a compound according to embodiment EE16 in a process for the preparation of the compound of formula (I) or the compound of formula (Ib).

EE18. The process according to embodiment E1 to EE8, and EE12 to EE15, wherein compound (Ib) is prepared by a process comprising the following step 3) reacting compound (A3) with a strong base, to afford compound (A4) according to the reaction scheme below

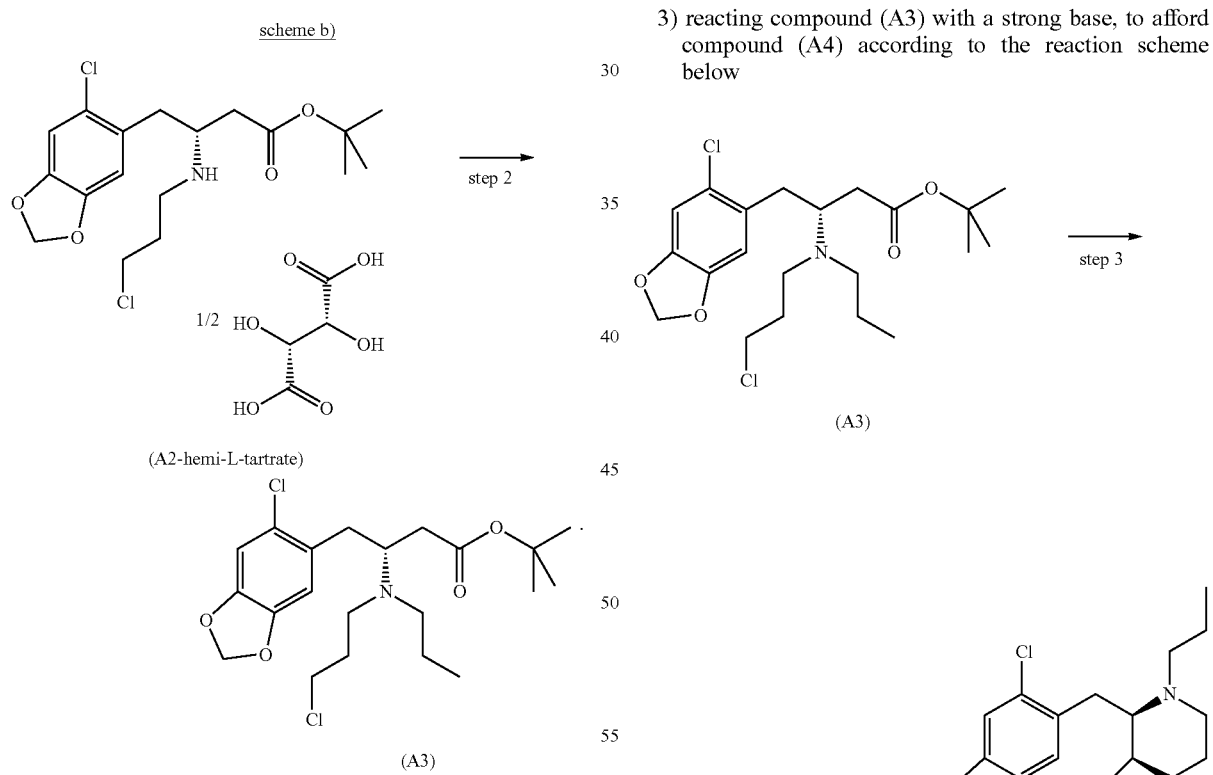

EE13. The process according to embodiment EE12, wherein compound (A3) is prepared by reacting compound (A2-hemi-L-tartrate) with propanal in the presence of a reducing agent.

EE14. The process according to embodiment EE13, wherein said reducing agent is selected from NaBH₃CN, sodium triacetoxyborohydride (STAB), borane, preferably 5-ethyl-2-methylpyridine borane (PEMB), or hydrogenation with a platinum catalyst, preferably platinum on carbon, and hydrogen gas.

optionally followed by isolating compound (A4) as a hemi-oxalate salt as depicted below

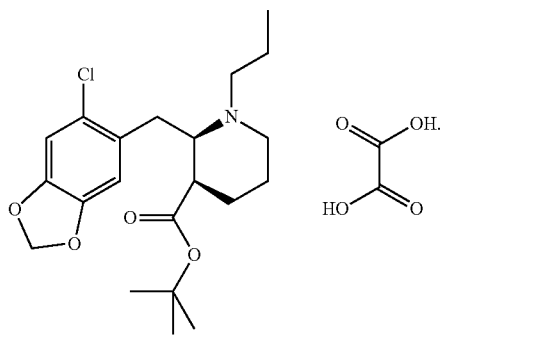

(A4-hemi-oxalate)

EE19. The process according to embodiment EE16, wherein said strong base is sodium bis(trimethylsilyl)amide (NaHMDS).

EE20. The process according to any of embodiments EE16 to EE17, wherein said reaction between compound (A3) and base takes place at a temperature in the range of −20 to −5° C., such as in the range of −15 to −5° C. or such as at a temperature of about −10° C.

EE21. The process according to any of embodiments EE16 to EE18, wherein said compound (A4) is mixed with oxalic acid and isolated as a hemi-oxalate salt.

EE22. The compound of formula (A4) below

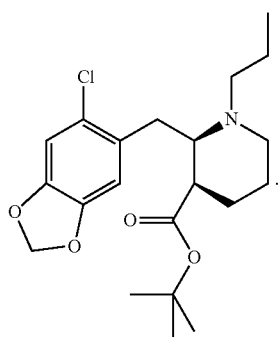

(A4)

or a salt thereof.

EE23. The compound of embodiment EE22 which is in the form of a hemi-oxalate salt as depicted below

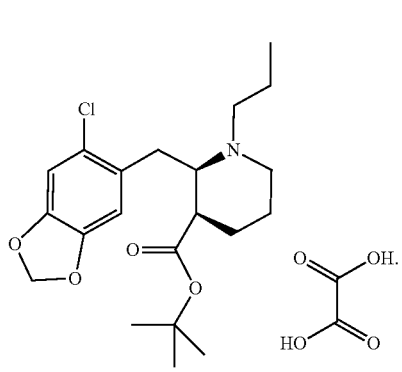

(A4-hemi-oxalate)

EE24. Use of a compound according to any of embodiments EE22 to EE23 for in a process for the preparation of the compound of formula (I) or the compound of formula (Ib).

EE25. The process according to embodiment EE1 to EE8, EE12 to EE15, EE18 to EE21, wherein compound (Ib) is prepared by a process comprising the following step 4) performing an intramolecular Friedel-Craft acylation of compound (A4) to afford compound (A5) according to the reaction scheme below

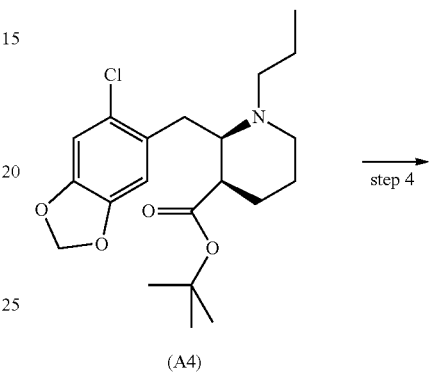

(A4)

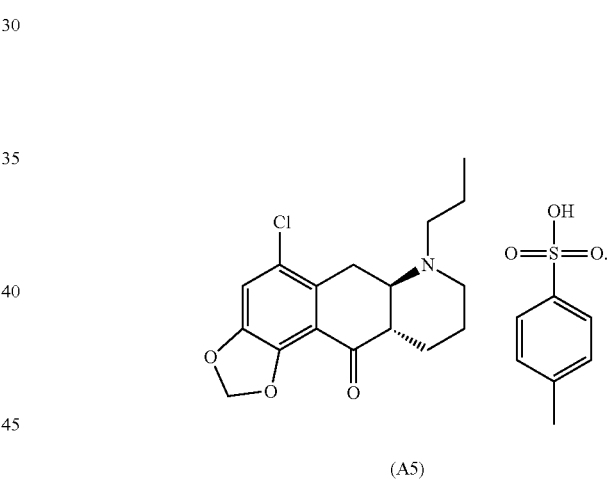

(A5)

optionally followed the step of isolating compound (A5) as a tosylate salt (A5-tosylate)

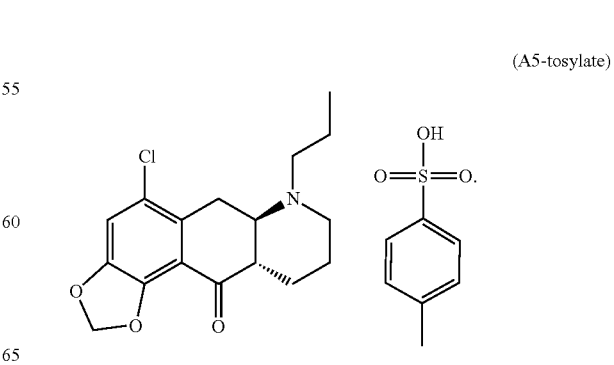

(A5-tosylate)

EE26. The compound of formula (A5) below

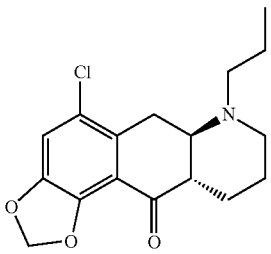

(A5)

or a salt thereof.

EE27. The compound of embodiment EE26 which is in the form of a tosylate salt as depicted below

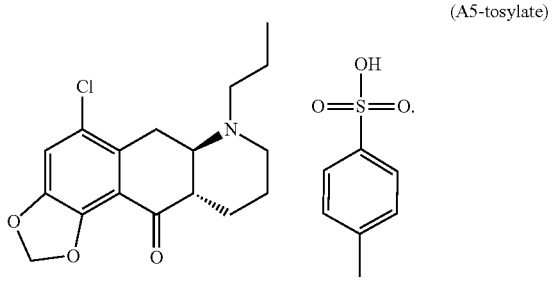

(A5-tosylate)

EE28. Use of a compound according to any of embodiments EE26 to EE27 in a process for the preparation of the compound of formula (I) or the compound of formula (Ib).

EE29. The process according to embodiment EE1 to EE8, EE12 to EE15, EE18 to EE21, and EE25, wherein compound (Ib) is prepared by a process comprising the following step 5) reducing compound (A5), or a salt thereof, to obtain compound (Ib), or a salt thereof according to the reaction scheme below

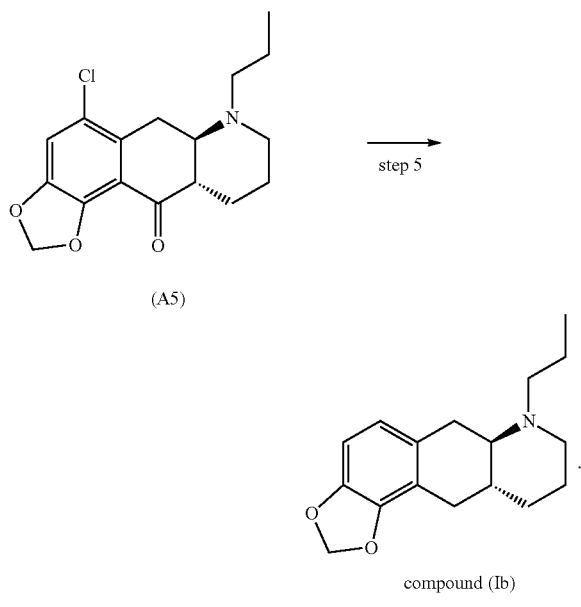

EE30. The process according to embodiment EE29, wherein said reduction takes place by use of a palladium catalyst.

EE31. The process according to embodiment 1, wherein compound (Ib) is prepared by a process comprising the following steps Step 0) according to any of embodiments EE1 to EE3; followed by step 1) according to any of embodiments EE1 and EE4 to EE8; followed by step 2) according to any of embodiments EE12 to EE15.

EE32. The process according to any one of embodiments EE1 to EE8, wherein compound (Ib) is prepared by a process comprising the following steps step 2) according to any of embodiments EE12 to EE15; followed by step 3) according to any of embodiments EE18 to EE21.

EE33. The process according to any one of embodiments EE1 to EE8, and EE12 to EE15, wherein compound (Ib) is prepared by a process comprising the following steps step 3) according to any of embodiments EE18-21; followed by step 4) according to embodiment EE25.

EE34. The process according to any one of the embodiments EE1 to EE8, wherein compound (Ib) is prepared by a process comprising the following steps step 4) according to any one of embodiments EE25; followed by step 5) according to any of embodiments EE29 to EE30.

EE35. The process according to embodiment 1, wherein compound (Ib) is prepared by a process comprising the following steps Step 0) according to any of embodiments EE1 to EE3; followed by step 1) according to any of embodiments EE1 and EE4 to EE8; followed by step 2) according to any of embodiments EE12 to EE15; followed by step 3) according to any of embodiments EE18-EE21.

EE36. The process according to embodiment 1, wherein compound (Ib) is prepared by a process comprising the following steps step 2) according to any of embodiments EE12 to EE15; followed by step 3) according to any of embodiments EE18-EE21; followed by step 4) according to embodiment EE25.

EE37. The process according to embodiment 1, wherein compound (Ib) is prepared by a process comprising the following steps step 3) according to any of embodiments EE18-EE21; followed by step 4) according to embodiment EE25; followed by step 5) according to any of embodiments EE29 to EE30.

EE38. The process according to embodiment 1, wherein compound (Ib) is prepared by a process comprising the following steps step 1) according to any of embodiments EE1 and EE4 to EE8; followed by step 2) according to any of embodiments EE12 to EE15; followed by step 3) according to any of embodiments EE18-EE21; followed by step 4) according to any one of embodiments EE25.

EE39. The process according to embodiment 1, wherein compound (Ib) is prepared by a process comprising the following steps step 2) according to any of embodiments EE12 to EE15; followed by
step 3) according to any of embodiments EE18-EE21; followed by
step 4) according to embodiment EE25; followed by
step 5) according to any of embodiments EE29 to EE30.

EE40. The process according to embodiment 1, wherein compound (Ib) is prepared by a process comprising the following steps
step 0) according to any of embodiments EE1 to EE3; followed by
step 1) according to any of embodiments EE1 and EE4 to EE8; followed by
step 2) according to any of embodiments EE12 to EE15; followed by
step 3) according to any of embodiments EE18-EE21; followed by
step 4) according to embodiment EE25; followed by
step 5) according to any of embodiments EE29 to EE30.

EE41. The process for the manufacture of compound (I) according to any of embodiments EE1-EE8, EE12-EE15, EE18-EE21, EE25, EE29-EE30, and EE32 to EE40 wherein compound (I) is prepared from compound (Ib) by the following step.

EE42. The process for the manufacture of compound (Ib) according to any one of the embodiments EE1-EE8, EE12-EE15, EE18-EE21, EE25, EE29-EE30, and EE32 to EE40, wherein the process is a chemical process ex vivo.

EE43. The process for the manufacture of compound (Ib) according to any one of the embodiments EE1-EE8, EE12-EE15, EE18-EE21, EE25, EE29-EE30, and EE31 to EE42, wherein said process is further defined by any one of the embodiments E48 to E82 and E85-E90.

EE44. A process for the manufacture of compound (Ib) with the formula below

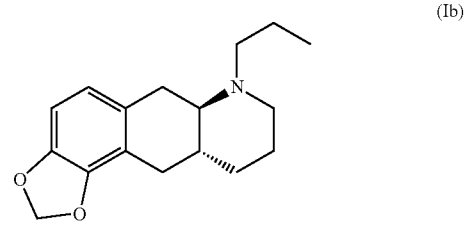 [SMILES: CCCN1CCC[C@@H]2Cc3c(ccc4c3OCO4)C[C@H]21]

wherein compound (Ib) is prepared by a process comprising the steps of:
Step 0)
Substep (S1) reacting compound (a6i) with tert-butyl 2-bromoacetate and zinc to form a mixture, followed by
treating the mixture from substep (S1) with acetic acid, followed by
reacting said mixture with 3-chloropropan-1-amine hydrochloride to afford compound (a2i); followed by
Step 1)
Substep (ii) reducing the compound (a2i) obtained in substep (S1) to obtain compound (a2ii), followed by
Substep (iii) resolving compound (a2ii) using L-tartaric acid to afford compound (A2-hemi-L-tartrate);
according to the reaction scheme below:

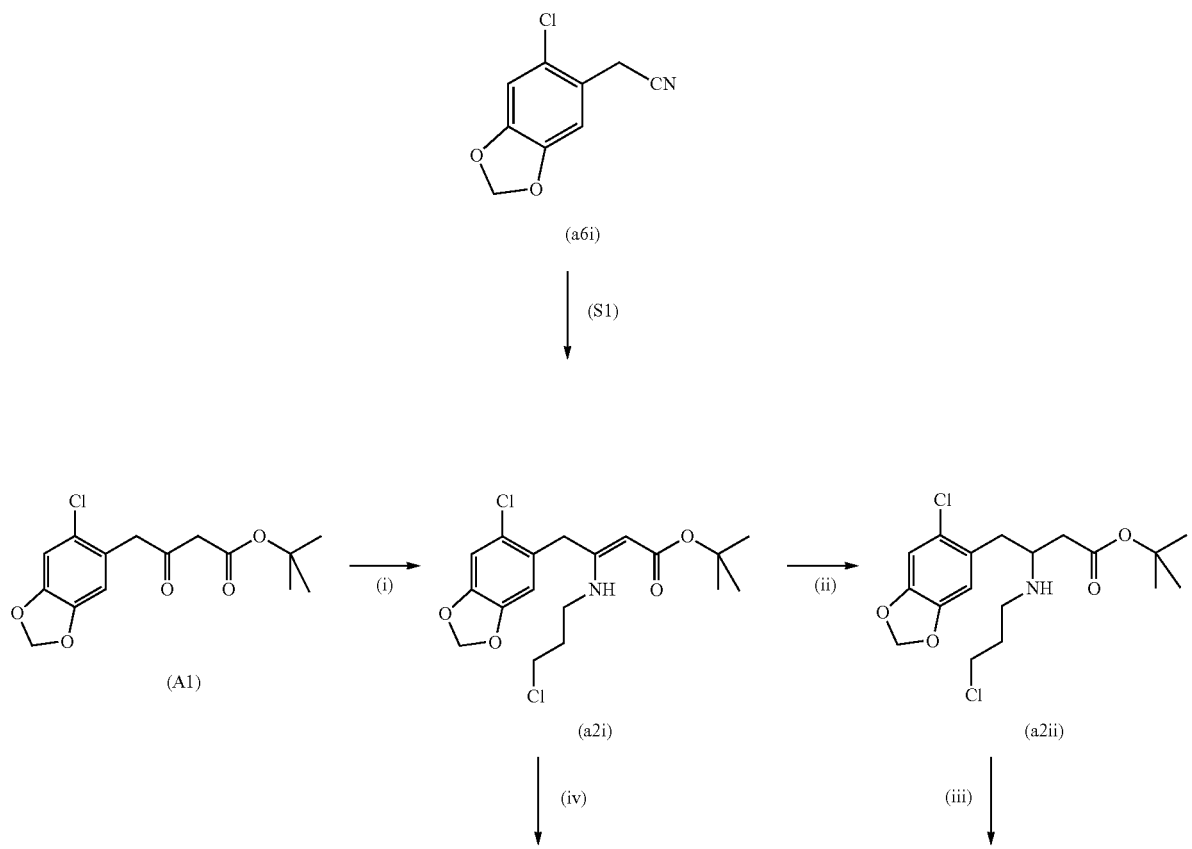

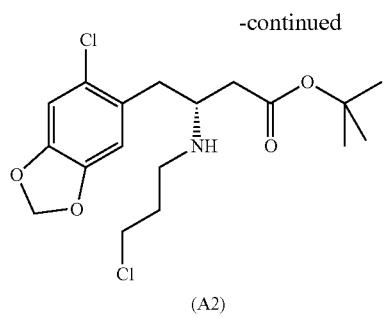

(A2)

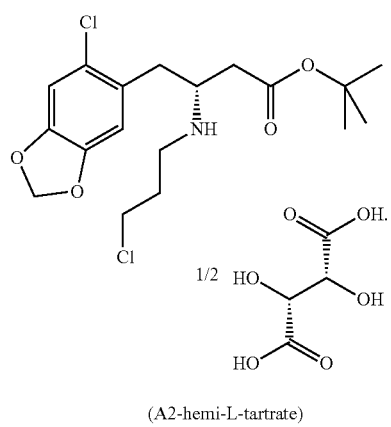

(A2-hemi-L-tartrate)

EE45. The process according to embodiment EE44, wherein the compound (a6i), or a salt thereof is prepared by a process comprising the step of reacting compound (a5i), or a salt thereof with a chlorinating agent

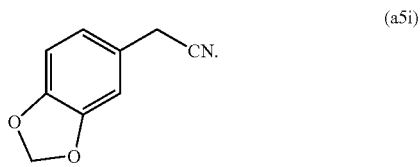 [SMILES: N#CCc1ccc2c(c1)OCO2]

(a5i)

EE46. The process according to embodiment EE45, wherein the chlorinating agent is sulfuryl chloride.

EE47. The process according to any one of embodiments EE44-E46 wherein compound (a2i) is isolated prior to initiating Step 1 substep (ii).

EE48. The process according to any one of embodiments EE44-EE47 further defined by any one of the embodiments E5-E7, E12-E16, E19-E22, E26, E30-E45, and E48-E82.

EE49. The process according to any one of embodiments EE44-EE48, wherein compound (A3) is prepared by a process comprising the following step
2) reacting compound (A2-hemi-L-tartrate) with propanal in the presence of a reducing agent, to afford compound (A3) according to reaction scheme b) below scheme b)

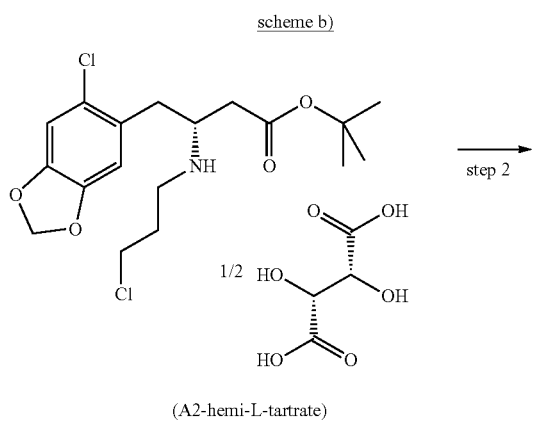

(A2-hemi-L-tartrate)

step 2

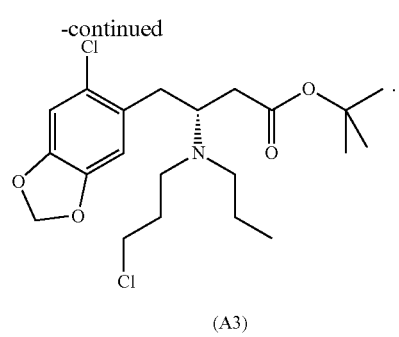

(A3)

Experimental Section

Abbreviations

DCM: Dichloromethane
DEA: Diethylamine
ee: Enantiomeric excess
EtOAc: Ethyl acetate
IPA: Isopropanol
iPrOAc: Isopropyl acetate
iPrOH: Isopropanol
Me-THF: 2-Methyltetrahydrofuran
NaHMDS: Sodium bis(trimethylsilyl)amide
Pd/C: Palladium on carbon
PEMB: 5-Ethyl-2-methylpyridine borane
STAB: Sodium triacetoxyborohydride
TFA: Trifluoroacetic acid
THF: Tetrahydrofuran
Me-THF: 2-Methyltetrahydrofuran
TsOH: p-Toluenesulfonic acid
v/v: Volume per volume
w/w: Weight per weight
NMR Methods
QNMR (600 MHz):

| | |
|---|---|
| 1) Relaxation delay | 40 sec |
| 2) Acquisition time | 3.76 sec |
| 3) Time domain | 64 k |
| 4) Size | 32 k |
| 5) Dummy scans | 4 |

-continued

| 6) Scans | 8 |
| 7) Pulse | 30 deg |

LC-MS and HPLC Methods

Analytical LC-MS data were obtained using the methods identified below.

LC-MS method: LC-MS were run on a Waters Aquity UPLC-MS system consisting of column manager, binary solvent manager, sample organizer, PDA detector (operating at 254 nM), ELS detector, and TO-MS equipped with APPI-source operating in positive ion mode.

LC-conditions: The column was Acquity UPLC BEH C18 1.7 µm; 2.1×150 mm operating at 60° C. with 0.6 mL/min of a binary gradient consisting of water+0.05% trifluoroacetic acid (A) and acetonitrile/water (95:5)+0.05% trifluoroacetic acid.

Gradient (linear):

| 0.00 min | 10% B |
| 3.00 min | 100% B |
| 3.60 min | 10% B |

Total run time: 3.6 minutes

Chiral HPLC method: Chiral HPLC were run on Merck Hitachi 7000 series HPLC consisting of pump, interface, programmable autosampler, column oven and UV detector (operating at 220 nm). The column was Chiralpak AD-H 5 µm; 4.6×250 mm operating at 30° C. with 1.0 mL/min flowrate of an eluent consisting of 90/10/0.1 hexane/IPA/DEA v/v, and a total run time of 20 minutes.

Example 1: Preparation of Compounds (a2i), (a2ii) and (A2-Hemi-L-Tartate) (Steps 0 Substep (i) Followed by Step 1 Substeps (ii) and (iii))

A mixture of 3-chloropropan-1-amine hydrochloride (24.9 g, 192 mmol), compound (A1) (20.0 g, 63.9 mmol), zinc chloride in Me-THF (1.7 ml, 3.20 mmol, 1.9 M), sodium acetate (17.3 g, 211 mmol) and sodium sulfate (4.54 g, 32.0 mmol) in Me-THF (150 mL) was stirred overnight.

Then a solution of sodium cyanoborohydride (5.22 g, 83 mmol) in Me-THF (50 mL) was added slowly at room temperature, and the mixture was stirred at 40° C. for 4 hours. The mixture was cooled to room temperature and added slowly to a stirred mixture of saturated aqueous $NH_4Cl$ solution (100 mL) and water (100 mL). The mixture was stirred for 15 minutes at room temperature. The organic phase was separated and washed with saturated aqueous $NH_4Cl$-water mixture (100 mL, 1:1 v/v), and then with saturated aqueous $NaHCO_3$ (2×100 mL) solution twice. The organic phase was washed with brine (100 mL), dried over $MgSO_4$, filtered and co-evaporated with MeOH in several rounds to dryness to yield crude compound (a2ii) (27.7 g) as an oil.

To a solution of the crude compound (a2ii) in MeOH (150 mL) was added with stirring at reflux a solution of L-tartaric acid (5.32 g, 35.5 mmol) in MeOH (43 mL). The mixture was allowed to cool slowly to room temperature overnight with stirring, and seeding (~20 mg) just below reflux. The obtained suspension was filtered, and the filter cake was washed with MeOH (20 mL) and dried in a vacuum oven at 40° C. to yield compound (A2-hemi-L-tartrate) (11.3 g, 38%) as a solid, with 1:161 S:R ratio (99.4% ee) of compound (A2) according to chiral HPLC analysis.

LC-MS: RT=2.22 minutes, $[M+H]^+$=390.0 m/z.

$^1$H NMR (600 MHz, DMSO-$d_6$) δ 7.03 (s, 1H), 6.95 (s, 1H), 6.04 (dd, J=1.0, 1.0 Hz, 2H), 4.12 (s, 2H, L-tartaric acid), 3.66 (t, J=6.5 Hz, 2H), 3.21 (quint, J=8.0 Hz, 1H), 2.91 (dd, J=6.0, 13.5 Hz, 1H), 2.75 (t, J=7.0 Hz, 2H), 2.62 (dd, J=8.5, 13.5 Hz, 1H), 2.31 (dd, J=7.0, 15.5 Hz, 1H), 2.26 (dd, J=7.0, 15.5 Hz, 1H), 1.82-1.86 (m, 2H), 1.36 (s, 9H).

Example 2: Preparation of Compound (A3) (Step 2)

A mixture of compound (A2-hemi-L-tartrate) (400 mg, 0.43 mmol), propanal (80 µL, 1.12 mol), acetic acid (49 µL, 0.86 mmol) and THF (4.0 mL) was stirred for 30 minutes. Then STAB (182 mg, 0.86 mmol) was added. The reaction mixture was stirred at room temperature for 3.5 hours. Saturated aqueous $NaHCO_3$ solution (4 mL) was added, and the mixture was extracted with toluene. The organic extract was dried over $MgSO_4$, filtered and evaporated to dryness to yield crude compound (A3) (167 mg, 90%) as a solid.

LC-MS: RT=2.46 minutes, $[M+H]^+$=432.3 m/z.

$^1$H NMR (600 MHz, CDCl$_3$) δ 6.80 (s, 1H), 6.62 (s, 1H), 5.94 (s, 2H), 3.49-3.55 (m, 2H), 3.35-3.39 (m, 1H), 2.90 (dd, J=3.5, 13.5 Hz, 1H), 2.61-2.63 (m, 2H), 2.52 (dd, J=9.0, 13.5 Hz, 1H), 2.36-2.45 (m, 3H), 2.16 (dd, J=5.5, 14.5 Hz, 1H), 1.86-1.92 (m, 1H), 1.76-1.83 (m, 1H), 1.39-1.49 (m, 2H), 1.41 (s, 9H), 0.86 (t, J=7.5 Hz, 3H).

Example 3: Preparation of Compound (A4) (Step 3)

To a solution of compound (A3) (40.0 g, 92.5 mmol) and toluene (311 mL) was added at −10° C. a solution of NaHMDS in THF (93.2 mL, 185 mmol, 2 M) over a period of 7.5 minutes. A slight increase in temperature was observed. The reaction mixture was stirred at −10° C. for 50 minutes. Then the temperature was raised to 5° C. and kept there overnight. The reaction mixture was then allowed reach room temperature, and an aqueous solution of NaCl (160 g, 5% w/w) was added over a period of 5 minutes. The organic phase was separated and evaporated to dryness in vacuum. The residue was stripped with acetone (200 mL), and the residue was mixed with acetone and oxalic acid (8.30 g, 92.2 mmol) and stirred overnight at room temperature. The mixture was then cooled on ice bath for 1 hour and filtered. The filter cake was washed with cold acetone (2×50 mL) twice, broken up and dried in vacuum at 50° C. to yield compound (A4-hemi-oxalate) (35.0 g, 78%) as a powder, exclusively as the cis isomer as determined by $^1$H NMR analysis.

LC-MS: RT=0.61 minutes, $[M+H]^+$=396.3 m/z.

$^1$H NMR (600 MHz, DMSO-$d_6$) δ 7.07 (s, 1H), 7.03 (s, 1H), 6.06 (s, 2H), 3.73 (br s, 1H), 2.99-3.16 (m, 2H), 2.73-2.90 (m, 4H), 2.43 (br s, 1H), 1.88-1.96 (m, 1H), 1.60-1.80 (m, 3H), 1.45-1.56 (m, 2H), 1.35 (s, 9H), 0.81 (t, J=7.5 Hz, 3H).

Example 4: Preparation of Compound (A5) (Step 4)

Free Basing of Compound (A4-Hemi-Oxalate):

A mixture of compound (A4-hemi-oxalate) (1000 g, 2.06 mol), heptane (8 L), water (6 L) and aqueous ammonia (500 mL, 6.76 mol, 25% w/w) was stirred for 4 hours at 35-45° C. The organic phase was separated and concentrated by distillation to 1-2 liters at >95° C. Then chlorobenzene (1.0

L) was added, and the mixture was concentrated by distillation in vacuum to 1.5-2.0 liters to yield a solution of compound (A4) as free base.

Formation of Compound (A5):

Trifluoroacetic acid (50.0 mL, 650 mmol) was added over a period of 5-15 minutes to a stirred mixture of $P_2O_5$ (30 g, 211 mmol) and chlorobenzene (200 mL) at 15-30° C. The resulting mixture was stirred for 30 minutes at room temperature.

Then a solution of compound (A4) as free base in chlorobenzene (see above, corresponding to 50 g of compound (A4-hemi-oxalate) (103 mmol)) was added at 25-45° C. over a period of 10-30 minutes. The resulting mixture was stirred at 35-40° C. for 3 hours, and then at room temperature overnight. To the reaction mixture was added IPA (125 mL) at room temperature, and the mixture was stirred at 40-45° C. for 2 hours, and then overnight at room temperature. The mixture was added over a period of 5-10 minutes to a stirred mixture of aqueous ammonia (150 mL, 2.00 mol, 25% w/w) and water (1.0 L) at 5-10° C. The mixture was stirred at 35-45° C. for 10 minutes. The organic phase was separated, and the aqueous phase was extracted with chlorobenzene (100 mL). To the stirred combined organic phases was added a solution of TsOH—$H_2O$ (23.6 g, 124 mmol) in IPA (150 mL). The mixture was concentrated on rotary evaporator in vacuum at 50-70° C. to volume of ~50 mL. IPA (100 mL) was added, and the mixture was concentrated again to ~50 mL on rotary evaporator in vacuum. IPA (125 mL) was added, and the mixture was stirred at room temperature to allow for precipitation. The formed suspension was cooled to 5° C., and filtered. The filter cake was washed with cold IPA (2×20 mL, 5° C.) twice, and dried in vacuum oven at 50° C. to yield compound (A5-tosylate) (35.6 g, 70%) as a powder.

LC-MS: RT=1.62 minutes, $[M+H]^+$=322.2 m/z.

$^1$H NMR (600 MHz, DMSO-$d_6$) δ 9.65 (br s, 1H), 7.46-7.48 (m, 2H), 7.45 (s, 1H), 7.09-7.11 (m, 2H), 6.23 (d, J=5.5 Hz, 1H), 6.21 (d, J=5.5 Hz, 1H), 3.67-3.74 (m, 1H), 3.56 (dd, J=4.5, 16 Hz, 2H), 3.31-3.39 (m, 1H), 3.06-3.14 (m, 1H), 2.93-3.03 (m, 1H), 2.83-2.93 (m, 2H), 2.27 (s, 3H), 2.18-2.24 (m, 1H), 1.91-1.98 (m, 1H), 1.70-1.84 (m, 2H), 1.61-1.70 (m, 1H), 1.41-1.50 (m, 1H), 0.96 (t, J=7.5 Hz, 3H).

Example 5: Preparation of Compound (Ib) (Step 5)

A mixture of compound (A5-tosylate) (5.00 g, 10.1 mmol), 5% Pd/C (561 mg, 0.101 mmol, Johnson Matthey type 424) and EtOH (50 mL) was hydrogenated at 4 bar hydrogen and 70° C. for 48 hours. The reaction mixture was filtered through Arbocell BC200, and the filtrate was co-evaporated with toluene several times. The resulting solution was washed with diluted aqueous ammonia (10% w/w), then with brine, dried over $MgSO_4$, filtered and evaporated to dryness to yield compound (Ib) (2.59 g) as a solid.

LC-MS: RT=1.95 minutes, $[M+H]^+$=274.3 m/z.

$^1$H NMR (600 MHz, CDCl$_3$) δ 6.63 (d, J=8.0 Hz, 1H), 6.59 (d, J=8.0 Hz, 1H), 5.92 (d, J=1.5 Hz, 1H), 5.89 (d, J=1.5 Hz, 1H), 3.15 (dd, J=5.0, 16.0 Hz, 1H), 2.97-3.00 (m, 1H), 2.82 (dd, J=5.0, 17.0 Hz, 1H), 2.73 (ddd, J=5.5, 10.5, 13.5 Hz, 1H), 2.56 (dd, J=11.0, 15.5 Hz, 1H), 2.49 (ddd, J=5.5, 10.5, 13.5 Hz, 1H), 2.21-2.30 (m, 1H), 2.18 (dt, J=5.0, 10.5 Hz, 1H), 1.87-1.92 (m, 1H), 1.58-1.72 (m, 2H), 1.42-1.58 (m, 1H), 1.06-1.15 (m, 1H), 0.89 (t, J=7.5 Hz, 3H).

Example 6: Preparation of Compound (I) from Compound (Ib) (Step 6)

A 2 L three-necked flask with a mechanical overhead stirrer was charged with the (−)-O,O'-di-p-toluoyl-L-tartaric acid salt (L-DTTA) salt of compound (Ib) (242 g, 367 mmol), toluene (1250 mL), water (375 mL) and 25% aqueous ammonia (100 mL, 1340 mmol). The mixture was stirred at 20-25° C. for 50 minutes before separation of the phases. The organic phase was washed with a mixture of water (170 mL) and 25% aqueous ammonia (35 mL, 470 mmol). The separated organic phase was at 50° C. concentrated under vacuum to near dryness. The residue was at 50° C. concentrated under vacuum to near dryness three times with toluene (3×250 mL), successively. The residue was dissolved and transferred to a 4 L three-necked flask with toluene (1200 mL). The solution was cooled to 4° C. and during 25 minutes $BCl_3$ in toluene (800 mL, 800 mmol, 1 M) was added. The reaction mixture was stirred for 3 hours at 0-5° C. After another 1.8 hours at 0-5° C. the reaction mixture was quenched with the addition of methanol (500 mL) over 20 minutes. The resulting mixture was heated overnight at 55° C. and then heated to reflux, where 500 mL of solvent was distilled off. Methanol (500 mL) was added and the mixture was heated to reflux, where 500 mL of solvent was distilled off. IPA (500 mL) was added and the mixture was heated to reflux, where 500 mL of solvent was distilled off. IPA (1200 mL) was added and the mixture was heated to 75° C. for 1.5 hours. The suspension was cooled to 20° C. in 1.5 hours and then the product was filtered off. The filter cake was washed two times with IPA/toluene (1:1, 2×200 mL). Drying at 50° C. under vacuum afforded the HCl salt of compound (I) (105 g, 96%) as a solid.

$^1$H NMR (600 MHz, DMSO-$d_6$) δ 6.53 (d, J=8.0 Hz, 1H), 6.37 (d, J=8.0 Hz, 1H), 3.01 (dd, J=4.5, 15.0 Hz, 1H), 2.89 (app d, J=11.0 Hz, 1H), 2.79 (dd, J=5.0, 17.5 Hz, 1H), 2.65-2.70 (m, 1H), 2.36 (dd, J=11.0, 15.5 Hz, 1H), 2.25-2.30 (m, 1H), 2.12 (dt, J=2.5, 12.0 Hz, 1H), 1.99-2.05 (m, 2H), 1.79-1.84 (m, 1H), 1.58-1.63 (m, 1H), 1.49-1.57 (m, 1H), 1.35-1.47 (m, 3H), 1.05 (dq, J=4.0, 13.0 Hz, 1H), 0.84 (t, J=7.5 Hz, 3H).

Example 7: Preparation of Compound (A2-Hemi-L-Tartate) from Compound (a2i) (Step 1 Substep (ii) Using a Pt Catalyst and Step 1 Substep iii)

A mixture of compound (a2i) (12.4 g, 32.0 mmol) and platinum on carbon (Johnson Matthey type 128M; 4.88% Pt; 52.6% w/w water; 2.16 g, 0.256 mmol) in Me-THF (31 mL) was hydrogenated at 60° C. and 4 bar hydrogen for 24 hours. The reaction mixture was filtered and evaporated to dryness to yield crude compound (a2ii). To the crude compound (a2ii) in MeOH (67 mL) was added slowly with stirring at reflux a solution of L-tartaric acid (2.40 g, 16.0 mmol) in MeOH (20 mL). The mixture was allowed to cool slowly to room temperature overnight with stirring, with seeding (~20 mg of pure compound (A2-hemi-L-tartrate)) at ~62° C. The obtained suspension was filtered, and the filter cake was washed with MeOH (10 mL), and dried in vacuum oven at 40° C. to yield compound (A2-hemi-L-tartrate) (4.90 g, 33%) as a white solid, with 99.2% enantiomeric excess of compound (A2) according to chiral HPLC analysis.

Example 8: Preparation of Compound (A1) from Compound (a6i) (Substep 0')

To vigorously stirred zinc powder (Umicore) (2.84 g, 43.5 mmol) in THF (15.0 mL) was added methanesulfonic acid (83 μL, 1.28 mmol) The mixture was heated at reflux for 30 minutes. Then a solution of compound (a6i) (5.00 g, 25.6 mmol) in THF (15.0 mL) was added, followed by the dropwise addition of tert-butyl 2-bromoacetate (6.48 g, 33.2 mmol) over a period of 1 hours and 40 minutes at reflux. The mixture was stirred at reflux for 1 hour, and the heating was removed, and the stirred reaction mixture was cooled to room temperature overnight. The reaction mixture was added with stirring to aq. HCl (38 mL, 76 mmol, 2.0 M) at 0° C. The resulting mixture was concentrated under vacuum to remove most THF, and then cooled in ice-water bath with vigorous stirring and seeding with pure sample of compound (A1).

The formed suspension was filtered cold (~5° C.), and the filter cake was washed with a 10:1 water:THF mixture and dried in a vacuum oven at 40° C. overnight to yield compound (A1) (7.72 g, 97%) as a slightly yellowish solid.

LC-MS (method: 555) RT=2.84 and 3.41 minutes (the two peaks are keto and enol tautomer of compound (A1))

$^1$H NMR (600 MHz, DMSO-$d_6$) δ 7.07 (s, 1H), 6.89 (s, 1H), 6.06 (s, 2H), 3.90 (s, 2H), 3.53 (s, 2H), 1.41 (s, 9H).

Example 9: Preparation of Compound (a2i) from Compound (a6i) (Step 0 Substep S1)

A mixture of zinc powder (Umicore) (10.0 g, 153 mmol) and methane sulfonic acid (332 µL, 5.11 mmol) in THF (60 mL) was heated at reflux for 30 minutes with stirring.

A solution of compound (a6i) (20.0 g, 102 mmol) in THF (60 mL) was added. Then tert-butyl 2-bromoacetate (25.9 g, 133 mmol) was added at reflux slowly over a period of 2 hours. The reaction mixture was stirred at reflux for 2 hours. The reaction mixture was cooled to room temperature.

The reaction mixture was filtered from excess zinc and cooled in an ice-water bath. Then acetic acid (7.6 mL, 133 mmol) was added slowly with stirring. The mixture was co-evaporated with MeOH several times, as to remove THF via the THF-MeOH azeotrope. This yielded a suspension to which a solution of 3-chloropropan-1-amine hydrochloride (33.2 g, 256 mmol) in MeOH (50 mL) was added. The mixture was stirred overnight at room temperature. The mixture was filtered, and the filter cake was washed with little MeOH, and dried in a vacuum oven at 40° C. to yield compound (a2i) (32.0 g, 81%) as a white solid.

LC-MS (method: 555) RT=2.84 and 3.41 minutes (the two peaks are keto and enol tautomer of compound (A1) seen due to hydrolysis of compound (a2i) to compound (A1) upon LC-MS analysis).

$^1$H NMR (600 MHz, DMSO-$d_6$) δ 8.57 (t, J=6.5 Hz, 1H), 7.10 (s, 1H), 6.89 (s, 1H), 6.08 (s, 2H), 3.85 (s, 1H), 3.67 (t, J=6.5 Hz, 2H), 3.58 (s, 2H), 3.33 (q, J=6.5 Hz, 2H), 1.95 (q, J=6.5 Hz, 2H), 1.36 (s, 9H).

Example 10: Preparation of Compound (a6i) from Compound (a5i)

To a vigorously stirred mixture of compound (a5i) (30.0 g, 186 mmol) and n-heptane (200 mL) was added sulfuryl chloride (17.4 ml, 214 mmol) at 0° C. The cooling was removed, and the mixture was allowed to warm to room temperature with vigorous stirring. The mixture was stirred for 4 hours at room temperature. The formed suspension was filtered, and the precipitate was washed with heptane and dried in vacuum at 40° C. to afford compound (a6i) (33.4 g, 92%) as a white solid.

LC-MS (method: 555) RT=2.28 minutes, [M+H]$^+$=195.1 m/z.

$^1$H NMR (600 MHz, CDCl$_3$) δ 6.95 (s, 1H), 6.88 (s, 1H), 6.02 (s, 2H), 3.74 (s, 2H).

Example 11: Large-Scale Preparation of Compound A4-HCl from Compound A2-Hemi-L-Tartate (Steps 2 and 3)

To a 10° C. cold slurry containing compound (A2-hemi-1-tartrate) (750 g, 805.9 mmol, 1 equivalents) and sodium triacetoxyborohydride (597.8 g, 2820 mmol, 3.5 equivalents) in THF (3750 mL, 5 volumes) was added a cold (10° C.) solution of propionaldehyde (121.7 g, 150.2 mL, 2100 mmol, 2.6 equivalents) in THF (1500 mL, 2 volumes) over the course of 30 minutes. Subsequently, glacial acetic acid (169.4 g, 161.5 mL, 2820 mmol, 3.5 equivalents) was added at 21° C. over the course of 5 minutes and the reaction mixture was stirred at 23° C. overnight. Then, 10% of the volume was distilled off under vacuum at 25° C. before water (2250 mL, 3 volumes) was added and the solution was stirred at 22° C. for 1 hour. Next, toluene (2250 mL, 3 volumes) was added followed by the addition of 25% ammonia (880 mL, 1176 mmol, 14.6 equivalents) until pH 8 and the solution was stirred at 22° C. for 1 hour before the two phases were separated. The aqueous phase was extracted with toluene (2250 mL, 3 volumes) and the combined organic phases were washed with 7.5% brine (1500 mL, 2 volumes). The organic solution was concentrated fully under reduced pressure at 65° C. affording crude compound (A3) as an oil (696.9 g, 100%, HPLC 98.4 area %, RT 14.96 min).

To the crude compound (A3) (696.6 g, 805.9 mmol) was added toluene (6000 mL, 8 volumes) and the solution was cooled to 0° C. before 1 m NaHMDS in THF (3380 mL, 3380 mmol, 2.1 equivalents) was added over the course of 100 minutes in which the temperature of the mixture did not exceed 5° C. The reaction mixture was stirred at 2° C. for 3.5 hours before the solution was warmed to 20° C. over the course of 13 minutes. Then, the reaction mixture was quenched by the addition of 5% brine (3750 mL, 5 volumes) and the mixture was stirred for 10 minutes before the two phases were separated. The organic phase was washed sequentially with 10% acetic acid (2310 mL, 4030 mmol, 2.5 equivalents) and water (3750 mL, 5 volumes) before the organic phase was concentrated fully under reduced pressure at 60° C. Then, isopropanol (2250 mL, 3 volumes) was added and the organic phase was again concentrated fully under reduced pressure at 60° C. Subsequently, isopropanol (750 mL, 1 volume) was added and the solution was transferred to a premixed solution (22° C.—premixed for 1 hour) of isopropanol (750 mL, 1 volume), heptane (6000 mL, 8 volumes) and acetyl chloride (229.2 mL, 3220 mmol, 2 equivalents) and precipitation was observed. The mixture was stirred at 20° C. for 1 hour before the slurry was cooled to 4° C. over 30 minutes and stirred at this temperature for 80 minutes. Then, the product was filtered off and the filter cake was washed with cold (4° C.) heptane (750 mL, 1 volumes). The wet product was dried under vacuum at 50° C. overnight. This afforded compound (A4-HCl) (555.1 g, 80%) as a white powder.

HPLC purity: 99.3 area %, 99.2 w/w %.

$^1$H NMR (400 MHz, CDCl$_3$) δ 12.50 (s, 1H), 7.05 (s, 1H), 6.82 (s, 1H), 5.99 (m, 2H), 3.87 (dd, J=15.8, 6.7 Hz, 1H), 3.65 (m, 1H), 3.45 (m, 1H), 3.20 (ddd, J=11.0, 9.7, 4.4 Hz, 1H), 3.08 (tdd, J=12.7, 4.9, 2.5 Hz, 1H), 2.92 (m, 2H), 2.77 (tdd, J=12.0, 8.5, 3.1 Hz, 1H), 2.49 (m, 1H), 2.21 (m, 1H), 1.84 (m, 2H), 1.66 (dtd, J=13.5, 11.7, 4.0 Hz, 1H), 1.52 (m, 1H), 1.39 (s, 9H), 0.77 (t, J=7.3 Hz, 3H).

REFERENCE LIST

U.S. Pat. No. 4,543,256
WO 2001/078713

WO 02/100377
WO 2009/026934,
WO 2009/026935
WO2010/097092
Alexander et Crutcher, (1990) Trends in Neuroscience 13: 266-71;
Bibbiani et al., Chase Experimental Neurology (2005), 192: 73-78;
Brückner and co-workers in *Synthesis* 2008, 14: 2229-2246;
Campbell et al., Neuropharmacology (1982); 21(10): 953-961;
Cannon et al., J. Heterocyclic Chem. (1980); 17: 1633-1636;
Delong, (1990) Trends in Neuroscience 13: 281-5;
Fan et al., Bioorg. Med. Chem. Lett. 2008, 18: 6236-6239;
Gerfen et al, Science (1990) 250: 1429-32;
Giardina and Williams; CNS Drug Reviews (2001), Vol. 7 (3): 305-316);
Grosset et al., Acta Neurol Scand. (2013), 128:166-171;
Hauser et al., Movement Disorders (2016), Vol. 32 (9): 1367-1372;
Kotsuki et al., J. Org. Chem. 1992, 57: 5036-5040);
Liu et al., J. Med. Chem. (2006), 49: 1494-1498;
Liu et al., Bioorganic Med. Chem. (2008), 16: 3438-3444;
S. Nishimura, Wiley 2001, Handbook of heterogeneous hydrogenation;
Poewe et al., Nature Review, (2017) vol 3 article 17013: 1-21;
Sprenger and Poewe, CNS Drugs (2013), 27: 259-272;
Sozio et al., Exp. Opin. Drug Disc. (2012); 7(5): 385-406;
Stahl and Wermuth (Eds) "Handbook of Pharmaceutical salts. Properties, selection, and use", Wiley-VCH, 2008;

The invention claimed is:

1. A process for the manufacture of compound (I) with the formula below

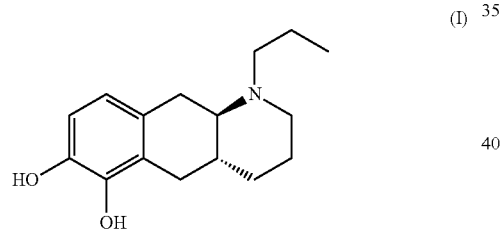

(I)

from the compound (Ib) with the formula below

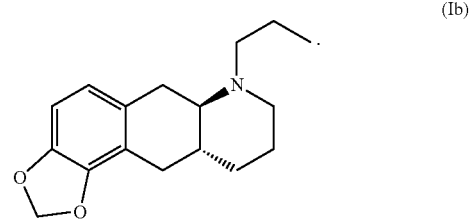 [SMILES: CCCN1CCC[C@@H]2Cc3c(ccc4c3OCO4)C[C@H]21]

(Ib)

wherein compound (Ib) is prepared by a process comprising the steps of:

Step 0)

Substep (i) reacting compound (A1) with 3-chloropropan-1-amine to obtain compound (a2i); or Substep (S1) reacting compound (a6i) with tert-butyl 2-bromoacetate and zinc to form a mixture, followed by treating the mixture from substep (S1) with acetic acid, followed by reacting said mixture with 3-chloropropan-1-amine hydrochloride to afford compound (a2i);

followed by

Step 1)

Substep (ii) reducing the compound (a2i) obtained in substep (i) or substep (S1) to obtain compound (a2ii), followed by Substep (iii) resolving compound (a2ii) using L-tartaric acid to afford compound (A2-hemi-L-tartrate);

or

Substep (i) or substep (S1) is followed by substep (iv) comprising the step of subjecting compound (a2i) to a hydrogenation performed with a chiral catalyst in the presence of hydrogen and a solvent to afford compound (A2);

according to the reaction scheme below:

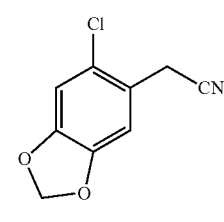

(a6i)

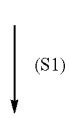

(S1)

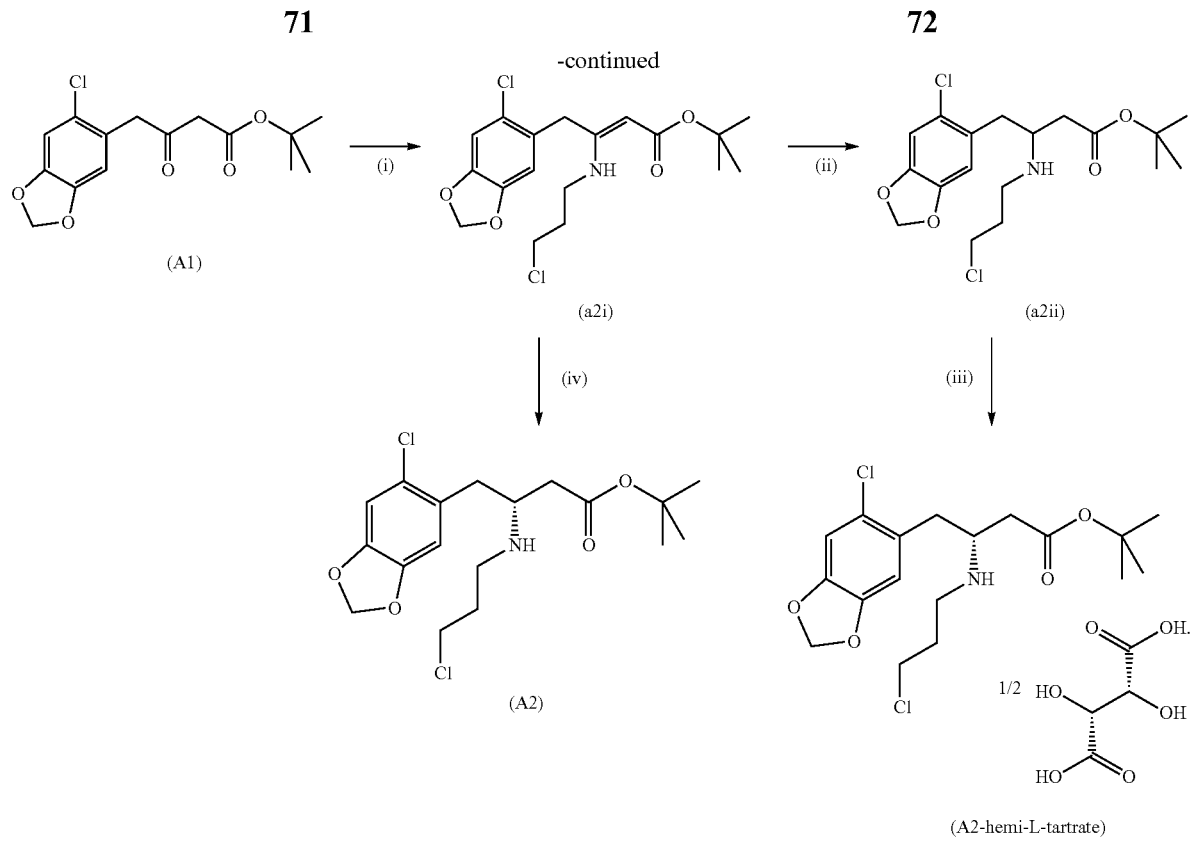

2. The process according to claim 1, wherein compound (Ib) is prepared by a process comprising the steps of:

Step 0)
Substep (S1)
  reacting compound (a6i) with tert-butyl 2-bromoacetate and zinc to form a mixture, followed by
  treating the mixture from substep (S1) with acetic acid, followed by
  reacting said mixture with 3-chloropropan-1-amine hydrochloride to afford compound (a2i);
followed by
Step 1)
Substep (ii) reducing the compound (a2i) obtained in substep (S1) to obtain compound (a2ii), followed by
Substep (iii) resolving compound (a2ii) using L-tartaric acid to afford compound (A2-hemi-L-tartrate).

3. The process according to claim 1, wherein the chiral catalyst in Step 1 substep (iv) is selected from (2S)-1-[(1S)-1-[bis(1,1-dimethylethyl)phosphino]ethyl]-2-(diphenylphosphino)ferrocene and bis(2,5-norbornadiene)rhodium (I) tetrafluoroborate.

4. The process according to claim 1, wherein the solvent in Step 1 substep (iv) is 2,2,2-trifluoroethanol.

5. The process according to claim 1, wherein the reduction in Step 1 substep (ii) takes place in the presence of a reducing agent selected from the group consisting of NaBH$_3$CN, sodium triacetoxyborohydride (STAB), a borane, 5-ethyl-2-methylpyridine borane (PEMB) and NaBH$_4$.

6. The process according to claim 1, wherein the reduction in Step 1 substep (ii) takes place by use of a platinum catalyst.

7. A process for the manufacture of compound (I):

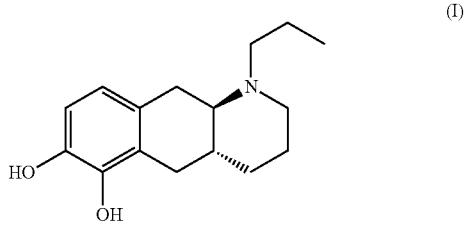 [SMILES: CCCN1CCC[C@@H]2Cc3c(ccc(O)c3O)C[C@H]21]

from compound (Ib):

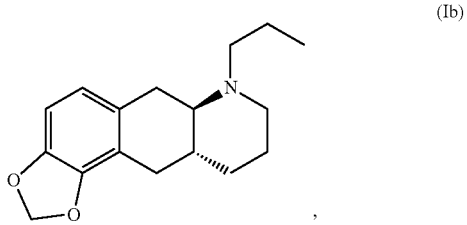 [SMILES: CCCN1CCC[C@@H]2Cc3c(ccc4c3OCO4)C[C@H]21]

wherein compound (Ib) is prepared by a process comprising the following step 2) reacting compound (A2) or compound (A2-hemi-L-tartrate) with propanal in the presence of a reducing agent,
to afford compound (A3) according to reaction scheme a) or b) below scheme a)
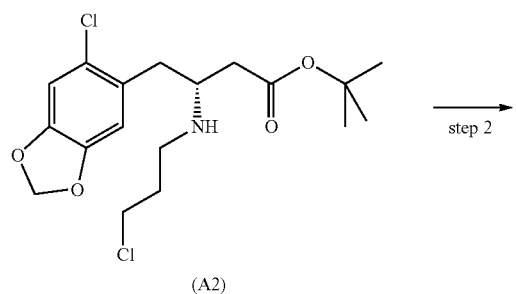
(A2)
scheme b)
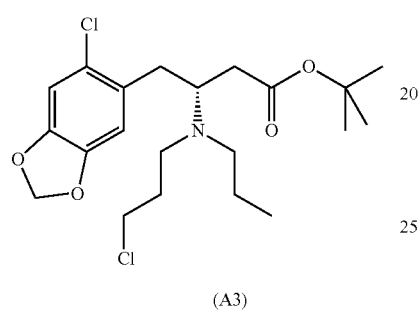
(A2-hemi-L-tartrate)
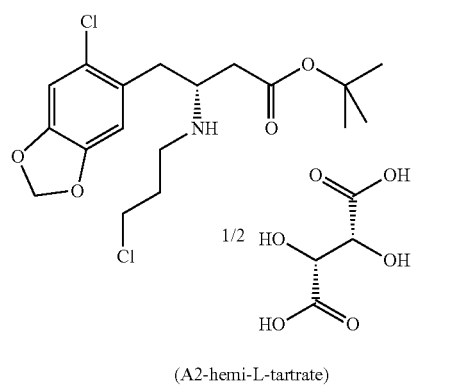
(A3)
8. A process for the manufacture of compound (I):
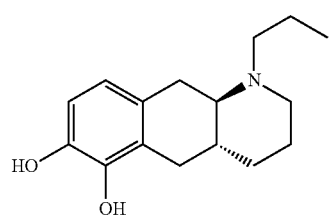
(I)
from compound (Ib):
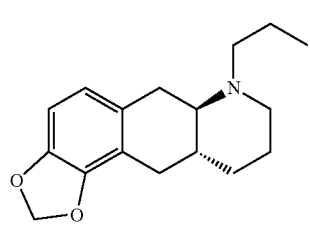
(Ib)
wherein compound (Ib) is prepared by a process comprising the following step
3) reacting compound (A3) with a strong base, to afford compound A4 according to the reaction scheme below
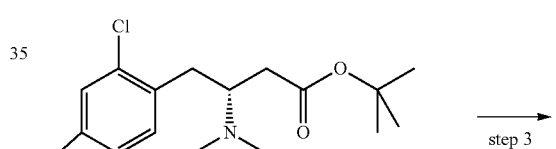
(A3)
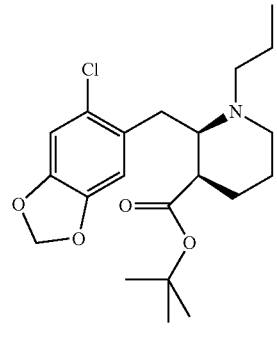
(A4)
optionally followed by isolating compound (A4), or a salt thereof.

9. The process according to claim 8, wherein A4 is isolated as a HCl salt as depicted below

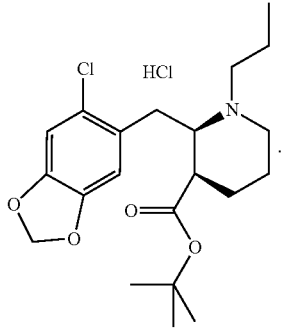

(A4-HCl)

10. A process for the manufacture of compound (I):

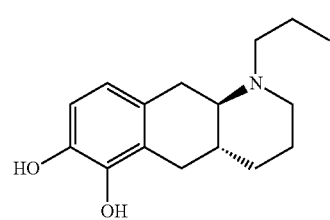

(I)

from compound (Ib):

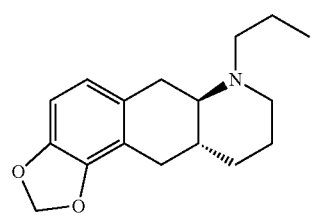

(Ib)

wherein compound (Ib) is prepared by a process comprising the following step
4) performing an intramolecular Friedel-Craft acylation of compound (A4) to afford compound (A5) according to the reaction scheme below:

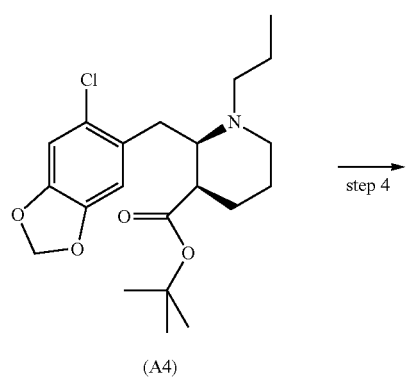

(A4)

-continued

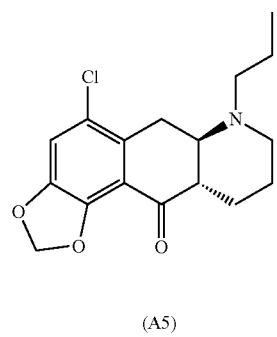

(A5)

optionally followed by isolating compound (A5), or a salt thereof.

11. A process for the manufacture of compound (I):

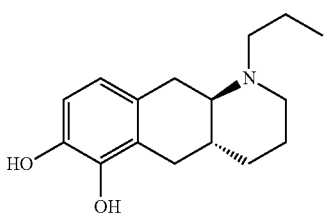

(I)

from compound (Ib):

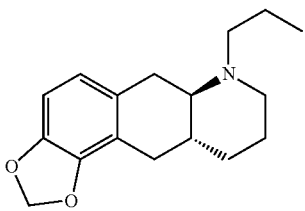

(Ib)

wherein compound (Ib) is prepared by a process comprising the following step
5) reducing compound (A5), or a salt thereof, to obtain compound (Ib), or a salt thereof according to the reaction scheme below

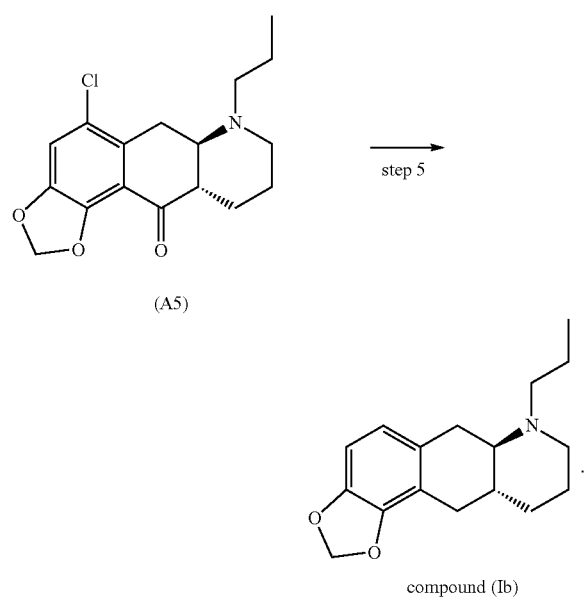

(A5)

compound (Ib)

to obtain compound (I) according to the reaction scheme below

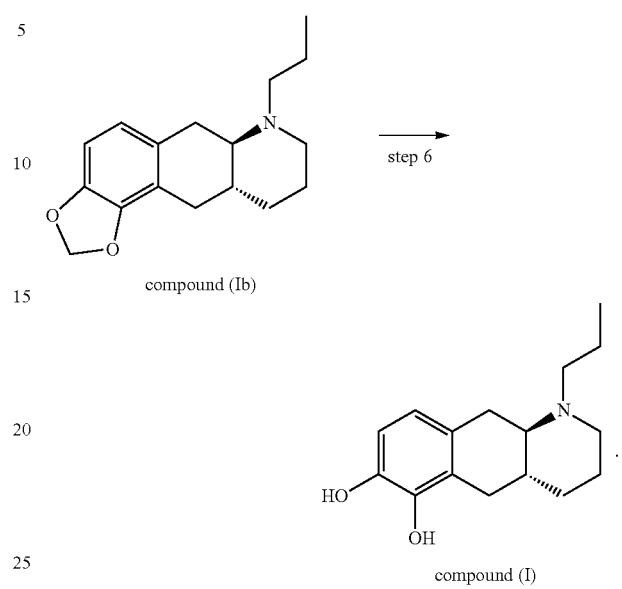

compound (Ib)

compound (I)

12. The process according to claim 11, wherein compound (I) is prepared from compound (Ib) by the following step 6) reacting compound (Ib) with a Lewis acid or Brønsted acid selected from the group consisting of $BCl_3$, $BBr_3$ and HBr, 13. The process according to claim 6, wherein the platinum catalyst is platinum on carbon.

* * * * *